(12) United States Patent
Tung et al.

(10) Patent No.: US 9,273,009 B2
(45) Date of Patent: *Mar. 1, 2016

(54) TETRAHYDRONAPHTHALENE DERIVATIVES

(71) Applicant: Concert Pharmaceuticals Inc., Lexington, MA (US)

(72) Inventors: Roger Tung, Lexington, MA (US); Craig E. Masse, Cambridge, MA (US); Julie F. Liu, Lexington, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/059,068
(22) Filed: Oct. 21, 2013
(65) Prior Publication Data

US 2014/0155444 A1 Jun. 5, 2014

Related U.S. Application Data

(63) Continuation of application No. 13/227,047, filed on Sep. 7, 2011, now Pat. No. 8,575,361, which is a continuation-in-part of application No. 13/038,533, filed on Mar. 2, 2011, now Pat. No. 8,513,434.

(60) Provisional application No. 61/351,500, filed on Jun. 4, 2010, provisional application No. 61/309,672, filed on Mar. 2, 2010.

(51) Int. Cl.
  *C07D 235/16* (2006.01)
  *A61K 31/4184* (2006.01)
  (Continued)

(52) U.S. Cl.
  CPC .......... *C07D 235/16* (2013.01); *A61K 31/4184* (2013.01); *A61K 45/06* (2013.01); *C07D 235/14* (2013.01)

(58) Field of Classification Search
  USPC ...................................................... 548/309.7
  See application file for complete search history.

(56) References Cited

U.S. PATENT DOCUMENTS

| 4,808,605 A | 2/1989 | Branca et al. |
| 5,811,557 A | 9/1998 | Wong et al. |

(Continued)

FOREIGN PATENT DOCUMENTS

| EP | 0268148 | 5/1988 |
| WO | WO 95/26325 | 10/1995 |

(Continued)

OTHER PUBLICATIONS

International Preliminary Report on Patentability in International Application No. PCT/US2012/053177, mailed Mar. 12, 2014, 7 pages.

(Continued)

*Primary Examiner* — Laura L. Stockton
(74) *Attorney, Agent, or Firm* — Fish & Richardson P.C.

(57) ABSTRACT

This invention relates to novel tetrahydronaphthalene derivatives, and pharmaceutically acceptable salts thereof according to the following formulae, in one embodiment:

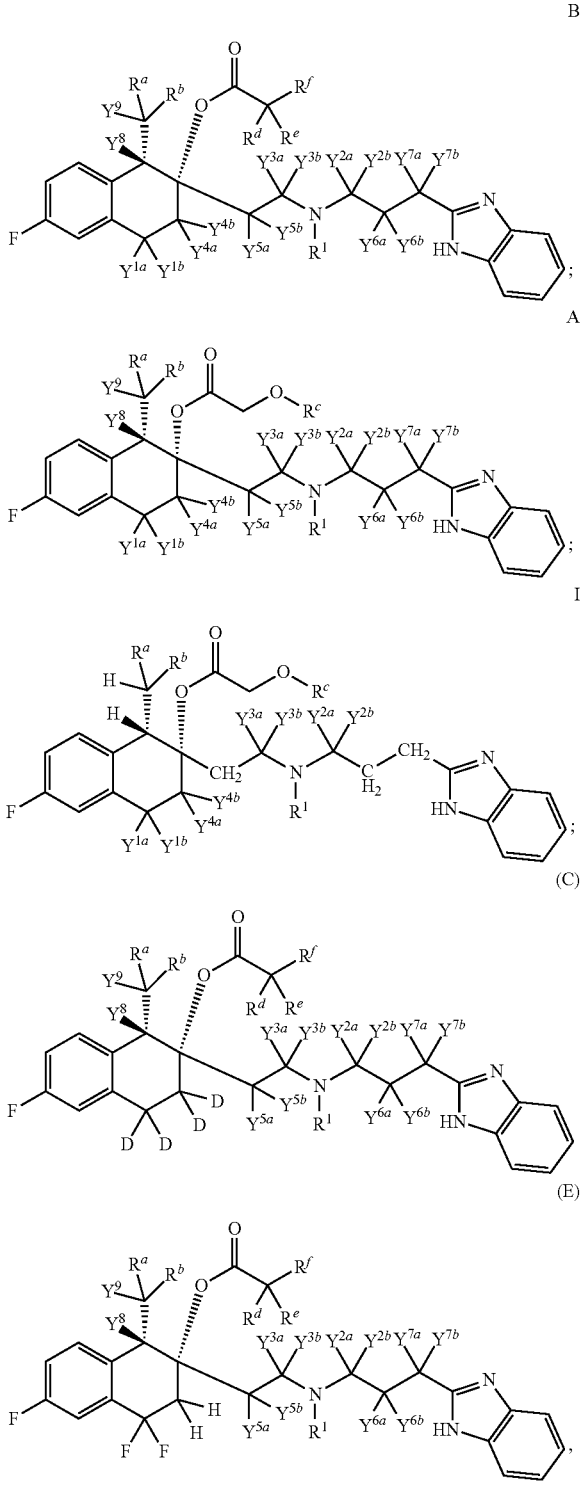

as described herein. This invention also provides compositions comprising a compound of this invention and the use of such compositions in methods of treating diseases and conditions that are beneficially treated by administering a selective T-type calcium channel blocker.

21 Claims, 1 Drawing Sheet

(51) Int. Cl.
C07D 235/14 (2006.01)
A61K 45/06 (2006.01)

(56) References Cited

U.S. PATENT DOCUMENTS

| | | | |
|---|---|---|---|
| 6,221,335 | B1 | 4/2001 | Foster |
| 6,410,743 | B2 | 6/2002 | Li et al. |
| 6,440,710 | B1 | 8/2002 | Keinan et al. |
| 6,603,008 | B1 | 8/2003 | Ando et al. |
| 7,517,990 | B2 | 4/2009 | Ito et al. |
| 2001/0041730 | A1 | 11/2001 | Li et al. |
| 2007/0082929 | A1 | 4/2007 | Gant et al. |
| 2007/0197695 | A1 | 8/2007 | Potyen et al. |
| 2008/0103122 | A1 | 5/2008 | Veltri |
| 2011/0237635 | A1 | 9/2011 | Tung et al. |

FOREIGN PATENT DOCUMENTS

| | | |
|---|---|---|
| WO | WO01/62741 | 8/2001 |
| WO | WO 2007/118651 | 10/2007 |
| WO | WO2010/046729 | 4/2010 |
| WO | WO2010/046855 | 4/2010 |
| WO | WO2011/109464 | 9/2011 |

OTHER PUBLICATIONS

U.S. Appl. No. 13/227,047, Tung et al.
"Mibefradil," Related Information [http://www.mims.com/USA/drug/info/mibefradil/mibefradil?type=full&mtype=generic], printed Oct. 14, 2011.
"Withdrawal of Posicor-TM (mibefradil) from the U.S. market," FDA Talk Paper, Roche Laboratories, Jun. 8, 1998, 4 pages.
International Search Report and Written Opinion for PCT/US2011/026787, mailed May 23, 2011.
Baille, T. A., "The Use of Stable Isotopes in Pharmacological Research," *Pharmacological Reviews*, 33(2): 81-132 (1981).
Bellosta et al. "Safety of Statins: Focus on Clinical Pharmacokinetics and Drug Interactions," *Circulation*, 2004, 109[suppl III]:III-50-III-57.
Browne, T. R., "Stable Isotope Techniques in Early Drug Development: An Economic Evaluation," *J. Clin. Pharmacol.*, 38: 213-220 (1998).
Cherrah, Y., et al., "Study of Deuterium Isotope Effects on Protein Binding by Gas Chromatography/Mass Spectrometry. Caffeine and Deuterated Isotopomers," *Biomedical and Environmental Mass Spectrometry*, 14: 653-657 (1987).
Du Souich et al., "Nonlinear kinetics and pharmacologic response to mibefradil," *Clin. Pharma. and Therapeutics*, 2000 67(3):249-257.
Dyck, L. E., et al., "Effects of Deuterium Substitution on the Catabolism of β-Phenylethylamine: An In Vivo Study," *Journal of Neurochemistry*, 46(2): 399-404 (1986).
Fisher, M.B. et al., "The Complexities Inherent in Attempts to Decrease Drug Clearance by Blocking Sites of CYP-Mediated Metabolism," *Curr. Opin. Drug Discov. Devel.*, 9(1):101-109 (2006).
Foster, A. B., "Deuterium Isotope Effects in Studies of Drug Metabolism," *Trends in Pharmacological Sciences*, 5: 524-527 (1984).
Foster, A. B., "Deuterium Isotope Effects in the Metabolism of Drugs and Xenobiotics: Implications for Drug Design," *Advances in Drug Research*, 14: 1-40 (1985).
Gouyette, A., "Synthesis of Deuterium-labelled Elliptinium and its Use in Metabolic Studies," *Biomedical and Environmental Mass Spectrometry*, 15: 243-247 (1988).
Harbeson et al. "Deuterium Medicinal Chemistry: Attenuation of Drug-Drug Interactions Arising from Mechanism-Based Inactivation of CYP Enzymes." Keystone Scientific Poster, Concert Pharmaceuticals, Inc., 2012, 1 page.
Haskins, N. J., "The Application of Stable Isotopes in Biomedical Research," *Biomedical Mass Spectrometry*, 9(7): 269-277 (1982).
Honma S., et al., "The Metabolism of Roxatidine Acetate Hydrochloride," *Drug Metabolism and Disposition*, 15(4): 551-559 (1987).
http://www.drugs.com/mmx/mibefradil-dihydrochloride.html, printed Feb. 12, 2012, 11 pages.
http://www.fda.gov/ohrms/dockets/ac/98/briefingbook/1998-3454B1_03_WL32, Jun. 1998, 17 pages.
http://www.sigmaaldrich.com, XtalFluor-M®—Sigma-Aldrich, printed Feb. 12, 2012, 2 pages.
http://www.sigmaaldrich.com/catalog/ProductDetail, XtalFluor-E®—Sigma-Aldrich, printed Feb. 12, 2012, 2 pages.
Huang et al. "NNC 55-0396 [(IS, 2S)-2-(2-N-[(3-Benzimidazol-2-yl)propyl]-N-methylamino )ethyl)-6-fluoro-1 ,2,3 ,4-tetrahydroo-1-isopropyl-2-naphthylcyclopropanecarboxylate dihydrochloride]: a new selective inhibitor of T-type calcium channels," *J. of Pharma. and Exp. Thera.*, 2004, 309(1):193-199.
International Preliminary Report on Patentability in International Application No. PCT/US2011/026787, issued Sep. 4, 2012, 8 pages.
International Search Report and Written Opinion in International Application No. PCT/US2012/053177, mailed Oct. 24, 2012, 12 pages.
Kushner, D.J. et al., "Pharmacological Uses and Perspectives of Heavy Water and Deuterated Compounds," *Can. J. Physiol. Pharmacol.*, 77:79-88 (1999).
Nuedexta FDA label, Highlights of Prescribing Information, marked by Avanir Pharmaceuticals, Inc., Aliso Viejo, CA, Issued Oct. 2010, 19 pages.
Orr et al. "Mechanism-Based Inactivation (MBI) of Cytochrome P450 Enzymes: Structure-Activity Relationships and Discovery Strategies to Mitigate Drug-Drug Interaction Risks," *J. Med. Chem.*, 2012, 55(11):4896-4933.
Pandya, "Old Drugs Yield New Discoveries: Case Studies of Site Selective Deuterium Incorporation," *Synthesis & Applications of Labelled Compounds, 20th International Isotope Soc. Symposium*, Oct. 18, 2011, 21 pages.
Park et al. "Contribution of cytochrome P450 3A4 and 3A5 to the metabolism of atorvastatin," *Xenobiotica*, 2008, 38(9):1240-1251.
Park et al., "Metabolism of Fluorine-Containing Drugs," *Annu. Rev. Pharmacol. Toxicol.*, 41:443-470 (2001).
Pieniaszek, H. J., et al., "Moricizine Bioavailability via Simultaneous, Dual, Stable Isotope Administration: Bioequivalence Implications," *J. Clin. Pharmacol*, 39: 817-825 (1999).
Quinidine Gluconate ER Tablets USA—printed Sep. 21, 2009, 2 pages.
Quinidine Sulfate-quinidine sulfate tablet, Watson Laboratories, Inc., Jun. 2009, 9 pages.
SoRelle, R. "Withdrawl of Posicor From Market," *Circulation*, 1998, 98:831-832.
Tonn G. R., et al., "Simultaneous Analysis of Diphenhydramine and a Stable Isotope Analog ($^2H_{10}$) Diphenhydramine Using Capillary Gas Chromatography with Mass Selective Detection in Biological Fluids from Chronically Instrumented Pregnant Ewes," *Biological Mass Spectrometry*, 22: 633-642 (1993).
Welker et al., "Single- and Multiple-dose Mibefradeil Pharmacokinetics in Normal and Hypertensive Subjects," *J. Pharm. Pharmacol.*, 50: 983-987 (1998).
Wiltshire et al., "Metabolism of the calcium antagonist, mibefradil (POSICOR®, Ro 40-5967). Part II. Metabolism in hepatic microsomes from rat, marmoset, cynomolgus monkey, rabbit and man," *Xenobiotica*, 27(6): 539-556 (1997).
Wiltshire et al., "Metabolism of the calcium antagonist, mibefradil (POSICOR™, Ro 40-5967). Part III. Comparative pharmacokinetics of mibefradil and its major metabolites in rat, marmoset, cynomolgus monkey and man," *Xenobiotica*, 27(6): 557-571 (1997).
Wolen, R. L., "The Application of Stable Isotopes to Studies of Drug Bioavailability and Bioequivalence," *J. Clin. Pharmacol.*, 26: 419-424 (1986).

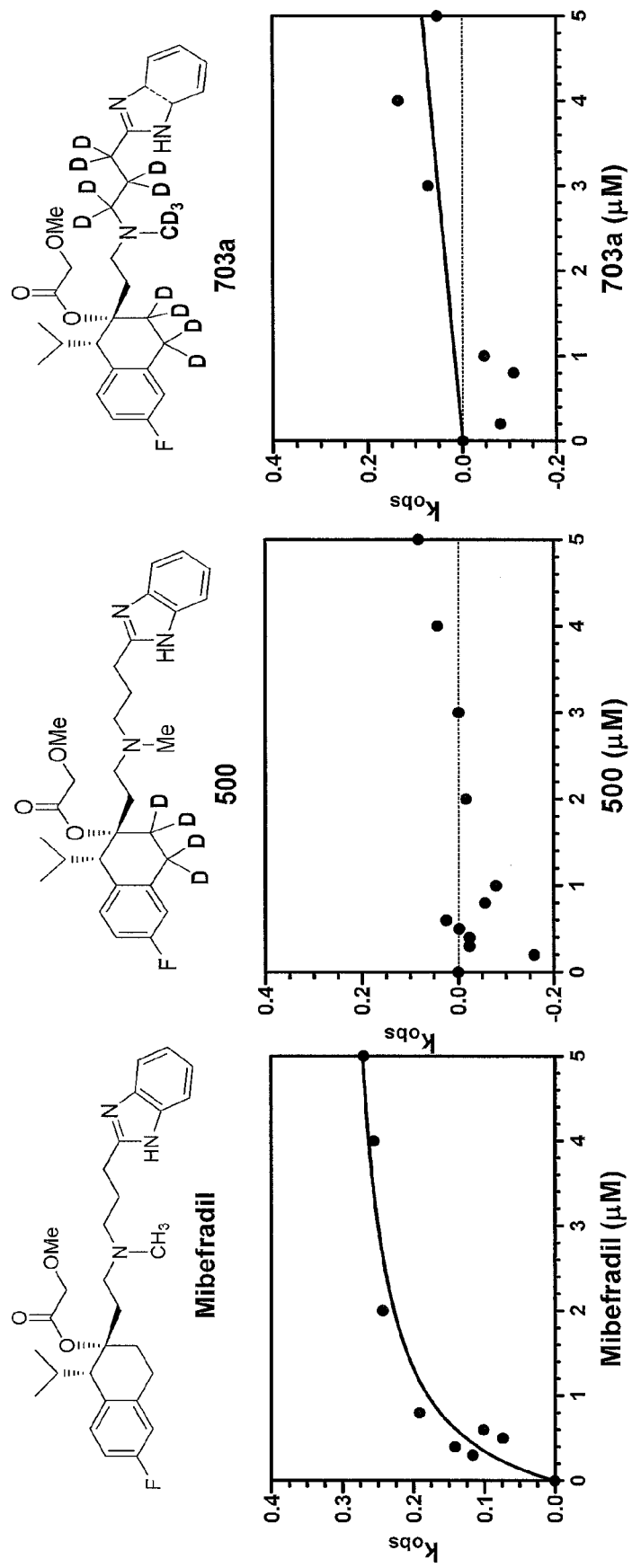

TETRAHYDRONAPHTHALENE DERIVATIVES

CROSS-REFERENCE TO RELATED APPLICATIONS

This application is a continuation of U.S. Utility application Ser. No. 13/227,047, filed Sep. 7, 2011 (now U.S. Pat. No. 8,575,361), which is a continuation-in-part of U.S. Utility application Ser. No. 13/038,533, filed Mar. 2, 2011 know U.S. Pat. No. 8,513,434), which claims priority under 35 U.S.C. §119(e) to U.S. Provisional Application No. 61/309,672, filed Mar. 2, 2010, and U.S. Provisional Application No. 61/351,500, filed Jun. 4, 2010. Each of the foregoing applications is incorporated by reference herein in its entirety.

BACKGROUND OF THE INVENTION

Many current medicines suffer from poor absorption, distribution, metabolism and/or excretion (ADME) properties that prevent their wider use or limit their use in certain indications. Poor ADME properties are also a major reason for the failure of drug candidates in clinical trials. While formulation technologies and prodrug strategies can be employed in some cases to improve certain ADME properties, these approaches often fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor patient compliance with the dosing regimen, side effects that become more acute with higher doses, and increased cost of treatment. A rapidly metabolized drug may also expose patients to undesirable toxic or reactive metabolites.

Another ADME limitation that affects many medicines is the formation of toxic or biologically reactive metabolites. As a result, some patients receiving the drug may experience toxicities, or the safe dosing of such drugs may be limited such that patients receive a suboptimal amount of the active agent. In certain cases, modifying dosing intervals or formulation approaches can help to reduce clinical adverse effects, but often the formation of such undesirable metabolites is intrinsic to the metabolism of the compound.

In some select cases, a metabolic inhibitor will be co-administered with a drug that is cleared too rapidly. Such is the case with the protease inhibitor class of drugs that are used to treat HIV infection. The FDA recommends that these drugs be co-dosed with ritonavir, an inhibitor of cytochrome P450 enzyme 3A4 (CYP3A4), the enzyme typically responsible for their metabolism (see Kempf, D. J. et al., Antimicrobial agents and chemotherapy, 1997, 41(3): 654-60). Ritonavir, however, causes adverse effects and adds to the pill burden for HIV patients who must already take a combination of different drugs. Similarly, the CYP2D6 inhibitor quinidine has been added to dextromethorphan for the purpose of reducing rapid CYP2D6 metabolism of dextromethorphan in a treatment of pseudobulbar affect. Quinidine, however, has unwanted side effects that greatly limit its use in potential combination therapy (see Wang, L et al., Clinical Pharmacology and Therapeutics, 1994, 56(6 Pt 1): 659-67; and FDA label for quinidine.

In general, combining drugs with cytochrome P450 inhibitors is not a satisfactory strategy for decreasing drug clearance. The inhibition of a CYP enzyme's activity can affect the metabolism and clearance of other drugs metabolized by that same enzyme. CYP inhibition can cause other drugs to accumulate in the body to toxic levels.

A potentially attractive strategy for improving a drug's metabolic properties is deuterium modification. In this approach, one attempts to slow the CYP-mediated metabolism of a drug or to reduce the formation of undesirable metabolites by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al, J Pharm Sci, 1975, 64:367-91; Foster, A B, Adv Drug Res 1985, 14:1-40 ("Foster"); Kushner, D J et al, Can J Physiol Pharmacol 1999, 79-88; Fisher, M B et al, Curr Opin Drug Discov Devel, 2006, 9:101-09 ("Fisher")). The results have been variable and unpredictable. For some compounds deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem. 1991, 34, 2871-76). Many drugs have multiple sites where metabolism is possible. The site(s) where deuterium substitution is required and the extent of deuteration necessary to see an effect on metabolism, if any, will be different for each drug.

This invention relates to novel tetrahydronaphthalene derivatives, and pharmaceutically acceptable salts thereof. This invention also provides compositions comprising a compound of this invention and the use of such compositions in methods of treating diseases and conditions that are beneficially treated by administering a selective T-type calcium channel blocker.

Mibefradil also known as (1S,2S)-2-(2-((3-(2-benzimidazolylpropyl) methylamino)ethyl)-6-fluoro-1,2,3,4-tetrahydro-1-isopropyl-2-naphthyl methoxyacetate dihydrochloride is a calcium channel blocker that is known to selectively and potently block the T-type calcium channel and, through a de-esterified metabolite, to also block the L-type calcium channel (Massie, B. M., Am J Cardiol., 1997, Nov. 6, 80(9A): 23I-32I). The pharmacologic activity of the de-esterified metabolite is approximately 10% that of the parent.

Mibefradil has demonstrated strong blood pressure reducing effects in patients with mild, moderate and severe hypertension, with less peripheral edema effects than other calcium channel blockers (Lacourcière, Y. et al., Am J. Hypertens. 1997 February; 10(2):189-96;) and has proven effective at improving exercise tolerance and reducing ischemic episodes in patients with chronic stable angina (see Massie above). Mibefradil was approved by the FDA in 1997 for treatment of hypertension, angina and cardiac failure, then was voluntarily withdrawn in 1998 due to potent drug-drug interactions with other medications resulting largely from its strong CYP3A4/5 inhibition and potentially also due to PGP inhibition (Wandel, C. et al., Drug Metabolism and Disposition, 2000, 28(8): 895-898). Although the exact mechanism of CYP3A inhibition is not known, it has been suggested that it results from oxidation of the benzimidazole moiety of mibefradil (Fontan, E et al, Curr Drug Metab 2005, 6:413-43).

Mibefradil is known to undergo metabolism through two metabolic pathways: esterase-catalyzed hydrolysis of the ester side chain (producing an alcohol metabolite known as Ro 40-5966); and cytochrome P450 3A4-catalyzed oxidation. Plasma concentrations of the alcohol metabolite resulting from de-esterification increase during chronic dosing and exceed those of the parent mibefradil at doses of 100 mg. The pharmacologic effect of the metabolite is approximately 10% of that of the parent.

Mibefradil's and Ro-40-5966's CYP 3A4 metabolism occurs predominantly at two molecular sites, most prominently the benzylic site of the tetrahydronaphthalene, and also to a significant extent alpha to the tertiary amine leading to removal of the N-methyl or the propylbenzimidazole groups. CYP 3A4 catalyzed metabolism also occurs to a limited extent on the benzimidazole ring of mibefradil at both the 4- and 5-positions (Wiltshire, H. R. et al., Xenobiotica, 1997, 27(6): 539-556).

When administered intravenously to healthy male volunteers, mibefradil caused a dose-dependent increase in bilirubin in all cases, and a severe decrease in plasma haptoglobin in two cases (Kleinbloesem C. H. et al., Journal of Cardiovascular Pharmacology, 1995, 25(6): 855-858).

Despite the beneficial activities of mibefradil, there is a continuing need for new compounds to treat the aforementioned diseases and conditions.

DEFINITIONS

The term "treat" means decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

The term "carbocyclyl" refers to a monocyclic hydrocarbon ring system such as cycloalkyl and phenyl.

The term "cycloalkyl" refers to a monocyclic monovalent saturated or non-aromatic unsaturated hydrocarbon ring system. The term "$C_3$-$C_6$ cycloalkyl" refers to a cycloalkyl wherein the number of ring carbon atoms is from 3 to 6. More particular examples of cycloalkyl groups include, cyclopropyl, cyclobutyl, cyclopentyl, cyclohexyl, cyclopropenyl, cyclobuten-2-yl, cyclobuten-3-yl, etc.

The term "carbocyclic ring" refers to a saturated or non-aromatic unsaturated ring. The term "3-6-membered carbocyclic ring" refers to a carbocyclic ring wherein the number of ring carbon atoms is from 3 to 6. A carbocyclic ring may be a ring having, for example, two free valencies, which may be two free valencies at the same carbon, such as the following rings:

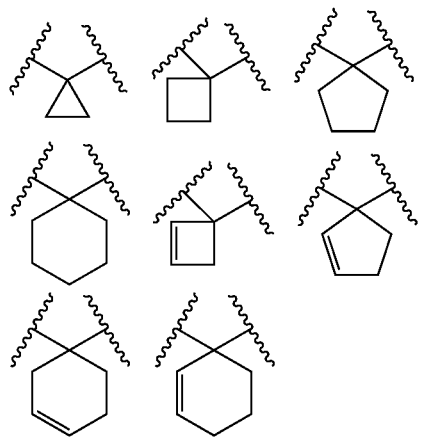

It will be recognized that some variation of natural isotopic abundance occurs in a synthesized compound depending upon the origin of chemical materials used in the synthesis. Thus, a preparation of mibefradil will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species in which the chemical structure differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The invention also provides salts of the compounds of the invention.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

Throughout the application all references to "a compound of Formula A" or "a compound of Formula I" or "a compound of Formula B" or "a compound of Formula B-I" or "a compound of Formula C" or "a compound of Formula E" or "a compound of the invention" or "a compound of claim" include, within the scope of each such term, synthetically feasible pharmaceutically acceptable salts of such a compound.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The compounds of the present invention (e.g., compounds of Formula B, B-I, A, C, E or Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "Tert" and "t-" each refer to tertiary. "US" refers to the United States of America.

"Substituted with deuterium" refers to the replacement of one or more hydrogen atoms with a corresponding number of deuterium atoms.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

BRIEF DESCRIPTION OF THE DRAWINGS

FIG. 1. CYP3A4 mechanism-based inhibition (MBI) in human liver microsomes (HLM) of Deuterated Mibefradil, compound 500 and compound 703a.

THERAPEUTIC COMPOUNDS

The present invention provides a compound of Formula B:

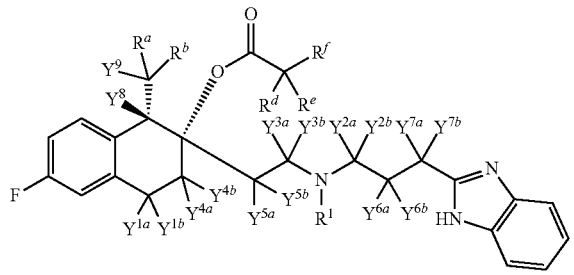

(B)

or a pharmaceutically acceptable salt thereof, wherein:
  $R^a$ and $R^b$ are each independently selected from —CH$_3$, —CDH$_2$, —CD$_2$H, and —CD$_3$;
  $R^d$ and $R^e$ are each independently hydrogen or deuterium; or $R^d$ and $R^e$ taken together with the carbon to which they are connected form a 3-6-membered carbocyclic ring that is optionally substituted with deuterium;
  provided that if $R^d$ and $R^e$ are each independently hydrogen or deuterium, then $R^f$ is $OR^c$ wherein $R^c$ is selected from —CH$_3$, —CDH$_2$, —CD$_2$H, and —CD$_3$;
  and provided that if $R^d$ and $R^e$ taken together with the carbon to which they are connected form a 3-6-membered carbocyclic ring, then $R^f$ is hydrogen or deuterium;
  $Y^{1a}$ and $Y^{1b}$ are each independently selected from hydrogen, deuterium and fluorine;
  $Y^{2a}$ and $Y^{2b}$ are each independently selected from hydrogen and deuterium;
  $Y^{3a}$ and $Y^{3b}$ are each independently selected from hydrogen and deuterium;
  $Y^{4a}$ and $Y^{4b}$ are each independently selected from hydrogen and deuterium;
  $Y^{5a}$ and $Y^{5b}$ are each independently selected from hydrogen and deuterium;
  $Y^{6a}$ and $Y^{6b}$ are each independently selected from hydrogen and deuterium;
  $Y^{7a}$ and $Y^{7b}$ are each independently selected from hydrogen and deuterium;
  $Y^8$ is selected from hydrogen and deuterium;
  $Y^9$ is selected from hydrogen and deuterium;
  and
  $R^1$ is selected from —CH$_3$, —CDH$_2$, —CD$_2$H, and —CD$_3$;
    provided that when each of $Y^{1a}$, $Y^{1b}$, $Y^{2a}$, $Y^{2b}$, $Y^{3a}$, $Y^{3b}$, $Y^{4a}$, $Y^{4b}$, $Y^{5a}$, $Y^{5b}$, $Y^{6a}$, $Y^{6b}$, $Y^{7a}$, $Y^{7b}$, $Y^8$, and $Y^9$ is hydrogen, $R^1$ comprises at least one deuterium.

In one embodiment, the present invention provides a compound of Formula A:

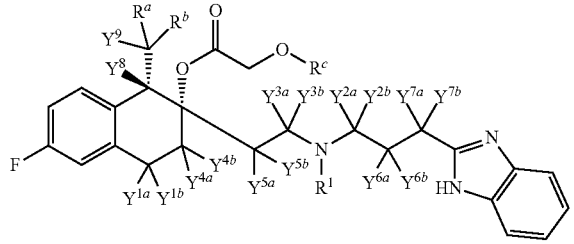

(A)

or a pharmaceutically acceptable salt thereof, wherein:
  $R^a$, $R^b$ and $R^c$ are each independently selected from —CH$_3$, —CDH$_2$, —CD$_2$H, and —CD$_3$;
  $Y^{1a}$ and $Y^{1b}$ are each independently selected from hydrogen, deuterium and fluorine;
  $Y^{2a}$ and $Y^{2b}$ are each independently selected from hydrogen and deuterium;
  $Y^{3a}$ and $Y^{3b}$ are each independently selected from hydrogen and deuterium;
  $Y^{4a}$ and $Y^{4b}$ are each independently selected from hydrogen and deuterium;
  $Y^{5a}$ and $Y^{5b}$ are each independently selected from hydrogen and deuterium;
  $Y^{6a}$ and $Y^{6b}$ are each independently selected from hydrogen and deuterium;
  $Y^{7a}$ and $Y^{7b}$ are each independently selected from hydrogen and deuterium;
  $Y^8$ is selected from hydrogen and deuterium;
  $Y^9$ is selected from hydrogen and deuterium;
  and
  $R^1$ is selected from —CH$_3$, —CDH$_2$, —CD$_2$H, and —CD$_3$;
    provided that when each of $Y^{1a}$, $Y^{1b}$, $Y^{2a}$, $Y^{2b}$, $Y^{3a}$, $Y^{3b}$, $Y^{4a}$, $Y^{4b}$, $Y^{5a}$, $Y^{5b}$, $Y^{6a}$, $Y^{6b}$, $Y^{7a}$, $Y^{7b}$, $Y^8$ and $Y^9$ is hydrogen, $R^1$ comprises at least one deuterium.

In one embodiment, the compound of Formula A is a compound of Formula I:

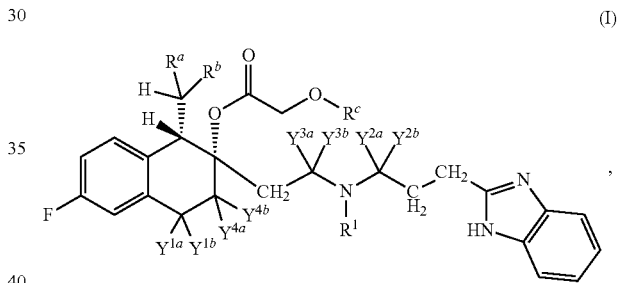

(I)

or a pharmaceutically acceptable salt thereof.

In one embodiment, the compound of Formula B is a compound of Formula B-I:

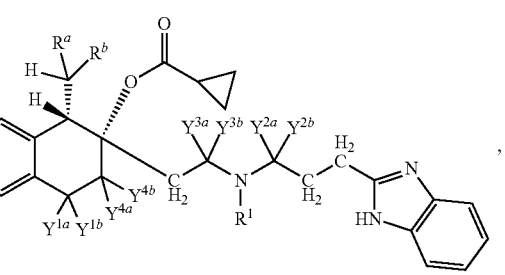

(B-I)

or a pharmaceutically acceptable salt thereof

In one embodiment of the compound of Formula I, $R^a$, $R^b$ and $R^c$ are each —CH$_3$; $Y^{1a}$ and $Y^{1b}$ are the same; $Y^{2a}$ and $Y^{2b}$ are the same; and $R^1$ is selected from —CH$_3$ and —CD$_3$. In one aspect of this embodiment $Y^{1a}$ and $Y^{1b}$ are each deuterium. In another aspect $Y^{1a}$ and $Y^{1b}$ are each hydrogen. In another aspect $Y^{1a}$ and $Y^{1b}$ are each fluorine. In one aspect of this embodiment, $Y^{2a}$ and $Y^{2b}$ are each deuterium. In another aspect $Y^{2a}$ and $Y^{2b}$ are each hydrogen. In one aspect of this embodiment, $R^1$ is —CH$_3$. In another aspect $R^1$ is —CD$_3$. In one aspect of this embodiment, $Y^{3a}$ and $Y^{3b}$ are each deuterium. In another aspect $Y^{3a}$ and $Y^{3b}$ are each hydrogen. In one aspect of this embodiment, when each of $Y^{1a}$, $Y^{1b}$, $Y^{2a}$ and $Y^{2b}$ is hydrogen, $R^1$ is —CD$_3$.

In one embodiment of the compound of Formula B-I, $R^a$ and $R^b$ are each —CH$_3$; $Y^{1a}$ and $Y^{1b}$ are the same; $Y^{2a}$ and $Y^{2b}$ are the same; and $R^1$ is selected from —CH$_3$ and —CD$_3$. In one aspect of this embodiment $Y^{1a}$ and $Y^{1b}$ are each deuterium. In another aspect $Y^{1a}$ and $Y^{1b}$ are each hydrogen. In another aspect $Y^{1a}$ and $Y^{1b}$ are each fluorine. In one aspect of this embodiment, $Y^{2a}$ and $Y^{2b}$ are each deuterium. In another aspect $Y^{2a}$ and $Y^{2b}$ are each hydrogen. In one aspect of this embodiment, $R^1$ is —CH$_3$. In another aspect $R^1$ is —CD$_3$. In one aspect of this embodiment, $Y^{3a}$ and $Y^{3b}$ are each deuterium. In another aspect $Y^{3a}$ and $Y^{3b}$ are each hydrogen. In one aspect of this embodiment, when each of $Y^{1a}$, $Y^{1b}$, $Y^{2a}$ and $Y^{2b}$ is hydrogen, $R^1$ is —CD$_3$.

In one embodiment of the compound of Formula I, $R^a$, $R^b$ and $R^c$ are each —CH$_3$; $Y^{1a}$ is fluorine; $Y^{1b}$ is selected from hydrogen and deuterium; $Y^{2a}$ and $Y^{2b}$ are the same; and $R^1$ is selected from —CH$_3$ and —CD$_3$. In one aspect of this embodiment $Y^{1b}$ is deuterium. In another aspect $Y^{1b}$ is hydrogen. In one aspect of this embodiment, $Y^{2a}$ and $Y^{2b}$ are each deuterium. In another aspect $Y^{2a}$ and $Y^{2b}$ are each hydrogen. In one aspect of this embodiment, $R^1$ is —CH$_3$. In another aspect $R^1$ is —CD$_3$. In one aspect of this embodiment, $Y^{3a}$ and $Y^{3b}$ are each deuterium. In another aspect $Y^{3a}$ and $Y^{3b}$ are each hydrogen.

In one embodiment of the compound of Formula B-I, $R^a$ and $R^b$ are each —CH$_3$; $Y^{1a}$ is fluorine; $Y^{1b}$ is selected from hydrogen and deuterium; $Y^{2a}$ and $Y^{2b}$ are the same; and $R^1$ is selected from —CH$_3$ and —CD$_3$. In one aspect of this embodiment $Y^{1b}$ is deuterium. In another aspect $Y^{1b}$ is hydrogen. In one aspect of this embodiment, $Y^{2a}$ and $Y^{2b}$ are each deuterium. In another aspect $Y^{2a}$ and $Y^{2b}$ are each hydrogen. In one aspect of this embodiment, $R^1$ is —CH$_3$. In another aspect $R^1$ is —CD$_3$. In one aspect of this embodiment, $Y^{3a}$ and $Y^{3b}$ are each deuterium. In another aspect $Y^{3a}$ and $Y^{3b}$ are each hydrogen.

In one embodiment of the compound of Formula I, $R^a$, $R^b$ and $R^c$ are each —CH$_3$; and $R^1$ is selected from —CH$_3$ and —CD$_3$. In one aspect of this embodiment $R^1$ is —CH$_3$. In another aspect $R^1$ is —CD$_3$. In one aspect of this embodiment, $Y^{2a}$ and $Y^{2b}$ are each deuterium. In another aspect $Y^{2a}$ and $Y^{2b}$ are each hydrogen. In one aspect of this embodiment, $Y^{3a}$ and $Y^{3b}$ are each deuterium. In another aspect $Y^{3a}$ and $Y^{3b}$ are each hydrogen.

In one embodiment of the compound of Formula B-I, $R^a$ and $R^b$ are each —CH$_3$; and $R^1$ is selected from —CH$_3$ and —CD$_3$. In one aspect of this embodiment $R^1$ is —CH$_3$. In another aspect $R^1$ is —CD$_3$. In one aspect of this embodiment, $Y^{2a}$ and $Y^{2b}$ are each deuterium. In another aspect $Y^{2a}$ and $Y^{2b}$ are each hydrogen. In one aspect of this embodiment, $Y^{3a}$ and $Y^{3b}$ are each deuterium. In another aspect $Y^{3a}$ and $Y^{3b}$ are each hydrogen.

In another set of embodiments, any atom not designated as deuterium in any of the embodiments set forth above is present at its natural isotopic abundance.

In one embodiment, the compound of Formula I is selected from any one of the compounds (Cmpd) set forth in Table 1a below, or a pharmaceutically acceptable salt thereof, wherein any atom not designated as deuterium in any of the compounds set forth therein is present at its natural isotopic abundance:

TABLE 1a

Examples of Compounds of Formula I wherein $R^a$, $R^b$ and $R^c$ are each —CH$_3$; each $Y^4$ is hydrogen; each $Y^1$ is the same; each $Y^2$ is the same; and each $Y^3$ is the same.

| Cmpd # | Each $Y^1$ | $R^1$ | Each $Y^2$ | Each $Y^3$ |
|---|---|---|---|---|
| 100 | D | CH$_3$ | H | H |
| 101 | D | CD$_3$ | H | H |
| 102 | D | CH$_3$ | D | H |
| 103 | D | CD$_3$ | D | H |
| 104 | F | CH$_3$ | H | H |
| 105 | F | CD$_3$ | H | H |
| 106 | F | CH$_3$ | D | H |
| 107 | F | CD$_3$ | D | H |
| 108 | H | CD$_3$ | H | H |
| 109 | H | CH$_3$ | D | H |
| 110 | H | CD$_3$ | D | H |
| 111 | D | CH$_3$ | H | D |
| 112 | D | CD$_3$ | H | D |
| 113 | D | CH$_3$ | D | D |
| 114 | D | CD$_3$ | D | D |
| 115 | F | CH$_3$ | H | D |
| 116 | F | CD$_3$ | H | D |
| 117 | F | CH$_3$ | D | D |
| 118 | F | CD$_3$ | D | D |
| 119 | H | CD$_3$ | H | D |
| 120 | H | CH$_3$ | D | D |
| 121 | H | CD$_3$ | D | D |

In one embodiment, the compound of Formula I is selected from any one of the compounds (Cmpd) set forth in Table 1b below, or a pharmaceutically acceptable salt thereof, wherein any atom not designated as deuterium in any of the compounds set forth therein is present at its natural isotopic abundance:

TABLE 1b

Examples of Compounds of Formula I wherein $R^a$, $R^b$ and $R^c$ are each —CH$_3$; each $Y^4$ is deuterium; each $Y^1$ is the same; each $Y^2$ is the same; and each $Y^3$ is the same.

| Cmpd # | Each $Y^1$ | $R^1$ | Each $Y^2$ | Each $Y^3$ |
|---|---|---|---|---|
| 500 | D | CH$_3$ | H | H |
| 501 | D | CD$_3$ | H | H |
| 502 | D | CH$_3$ | D | H |
| 503 | D | CD$_3$ | D | H |
| 504 | F | CH$_3$ | H | H |
| 505 | F | CD$_3$ | H | H |
| 506 | F | CH$_3$ | D | H |
| 507 | F | CD$_3$ | D | H |
| 508 | H | CD$_3$ | H | H |
| 509 | H | CH$_3$ | D | H |
| 510 | H | CD$_3$ | D | H |
| 511 | D | CH$_3$ | H | D |
| 512 | D | CD$_3$ | H | D |
| 513 | D | CH$_3$ | D | D |
| 514 | D | CD$_3$ | D | D |
| 515 | F | CH$_3$ | H | D |
| 516 | F | CD$_3$ | H | D |
| 517 | F | CH$_3$ | D | D |
| 518 | F | CD$_3$ | D | D |
| 519 | H | CD$_3$ | H | D |
| 520 | H | CH$_3$ | D | D |
| 521 | H | CD$_3$ | D | D |

In one embodiment, the compound of Formula A is selected from any one of the compounds (Cmpd) set forth in Table 1c below, or a pharmaceutically acceptable salt thereof, wherein any atom not designated as deuterium in any of the compounds set forth therein is present at its natural isotopic abundance:

TABLE 1c

Examples of Compounds of Formula A wherein $R^a$, $R^b$ and $R^c$ are each —$CH_3$; each $Y^4$ is deuterium; each $Y^1$ is the same; each $Y^2$ is the same; each $Y^3$ is the same; each $Y^5$ is hydrogen; each $Y^6$ is deuterium; each $Y^7$ is deuterium; each $Y^8$ is hydrogen; and each $Y^9$ is hydrogen:

| Cmpd # | Each $Y^1$ | $R^1$ | Each $Y^2$ | Each $Y^3$ |
|---|---|---|---|---|
| 600 | D | $CH_3$ | H | H |
| 601 | D | $CD_3$ | H | H |
| 602 | D | $CH_3$ | D | H |
| 603 | D | $CD_3$ | D | H |
| 604 | F | $CH_3$ | H | H |
| 605 | F | $CD_3$ | H | H |
| 606 | F | $CH_3$ | D | H |
| 607 | F | $CD_3$ | D | H |
| 608 | H | $CD_3$ | H | H |
| 609 | H | $CH_3$ | D | H |
| 610 | H | $CD_3$ | D | H |
| 611 | D | $CH_3$ | H | D |
| 612 | D | $CD_3$ | H | D |
| 613 | D | $CH_3$ | D | D |
| 614 | D | $CD_3$ | D | D |
| 615 | F | $CH_3$ | H | D |
| 616 | F | $CD_3$ | H | D |
| 617 | F | $CH_3$ | D | D |
| 618 | F | $CD_3$ | D | D |
| 619 | H | $CD_3$ | H | D |
| 620 | H | $CH_3$ | D | D |
| 621 | H | $CD_3$ | D | D |

In one embodiment, the compound of Formula I is selected from any one of the compounds (Cmpd) set forth in Table 2 below, or a pharmaceutically acceptable salt thereof, wherein any atom not designated as deuterium in any of the compounds set forth therein is present at its natural isotopic abundance:

TABLE 2

Examples of Compounds of Formula I wherein $R^a$, $R^b$ and $R^c$ are each —$CH_3$, $Y^{1a}$ is fluorine and $Y^{1b}$ is hydrogen or deuterium; each $Y^4$ is hydrogen; each $Y^2$ is the same; and each $Y^3$ is the same

| Cmpd # | $Y^{1b}$ | $R^1$ | Each $Y^2$ | Each $Y^3$ |
|---|---|---|---|---|
| 200 | D | $CH_3$ | H | H |
| 201 | D | $CD_3$ | H | H |
| 202 | D | $CH_3$ | D | H |
| 203 | D | $CD_3$ | D | H |
| 204 | H | $CH_3$ | H | H |
| 205 | H | $CD_3$ | H | H |
| 206 | H | $CH_3$ | D | H |
| 207 | H | $CD_3$ | D | H |
| 208 | D | $CH_3$ | H | D |
| 209 | D | $CD_3$ | H | D |
| 210 | D | $CH_3$ | D | D |
| 211 | D | $CD_3$ | D | D |
| 212 | H | $CH_3$ | H | D |
| 213 | H | $CD_3$ | H | D |
| 214 | H | $CH_3$ | D | D |
| 215 | H | $CD_3$ | D | D |

In one embodiment, the compound of Formula I is selected from any one of the compounds (Cmpd) set forth in Table 2 above, wherein the stereochemistry at the carbon bearing $Y^{1a}$ and $Y^{1b}$ is (R), or a pharmaceutically acceptable salt thereof, wherein any atom not designated as deuterium in any of the compounds set forth therein is present at its natural isotopic abundance.

In one embodiment, the compound of Formula I is selected from any one of the compounds (Cmpd) set forth in Table 2 above, wherein the stereochemistry at the carbon bearing $Y^{1a}$ and $Y^{1b}$ is (S), or a pharmaceutically acceptable salt thereof, wherein any atom not designated as deuterium in any of the compounds set forth therein is present at its natural isotopic abundance.

In one embodiment, the compound of Formula B-I is selected from any one of the compounds (Cmpd) set forth in Table 3 below, or a pharmaceutically acceptable salt thereof, wherein any atom not designated as deuterium in any of the compounds set forth therein is present at its natural isotopic abundance:

TABLE 3

Examples of Compounds of Formula B-I wherein $R^a$ and $R^b$ are each —$CH_3$; each $Y^4$ is hydrogen; each $Y^1$ is the same; each $Y^2$ is the same; and each $Y^3$ is the same.

| Cmpd # | Each $Y^1$ | $R^1$ | Each $Y^2$ | Each $Y^3$ |
|---|---|---|---|---|
| 300 | D | $CH_3$ | H | H |
| 301 | D | $CD_3$ | H | H |
| 302 | D | $CH_3$ | D | H |
| 303 | D | $CD_3$ | D | H |
| 304 | F | $CH_3$ | H | H |
| 305 | F | $CD_3$ | H | H |
| 306 | F | $CH_3$ | D | H |
| 307 | F | $CD_3$ | D | H |
| 308 | H | $CD_3$ | H | H |
| 309 | H | $CH_3$ | D | H |
| 310 | H | $CD_3$ | D | H |
| 311 | D | $CH_3$ | H | D |
| 312 | D | $CD_3$ | H | D |
| 313 | D | $CH_3$ | D | D |
| 314 | D | $CD_3$ | D | D |
| 315 | F | $CH_3$ | H | D |
| 316 | F | $CD_3$ | H | D |
| 317 | F | $CH_3$ | D | D |
| 318 | F | $CD_3$ | D | D |
| 319 | H | $CD_3$ | H | D |
| 320 | H | $CH_3$ | D | D |
| 321 | H | $CD_3$ | D | D |

In one embodiment, the compound of Formula B-I is selected from any one of the compounds (Cmpd) set forth in Table 4 below, or a pharmaceutically acceptable salt thereof, wherein any atom not designated as deuterium in any of the compounds set forth therein is present at its natural isotopic abundance:

TABLE 4

Examples of Compounds of Formula B-I wherein $R^a$ and $R^b$ are each —$CH_3$, $Y^{1a}$ is fluorine and $Y^{1b}$ is hydrogen or deuterium; each $Y^4$ is hydrogen; each $Y^2$ is the same; and each $Y^3$ is the same

| Cmpd # | $Y^{1b}$ | $R^1$ | Each $Y^2$ | Each $Y^3$ |
|---|---|---|---|---|
| 400 | D | $CH_3$ | H | H |
| 401 | D | $CD_3$ | H | H |
| 402 | D | $CH_3$ | D | H |
| 403 | D | $CD_3$ | D | H |
| 404 | H | $CH_3$ | H | H |
| 405 | H | $CD_3$ | H | H |
| 406 | H | $CH_3$ | D | H |
| 407 | H | $CD_3$ | D | H |
| 408 | D | $CH_3$ | H | D |
| 409 | D | $CD_3$ | H | D |
| 410 | D | $CH_3$ | D | D |
| 411 | D | $CD_3$ | D | D |
| 412 | H | $CH_3$ | H | D |
| 413 | H | $CD_3$ | H | D |
| 414 | H | $CH_3$ | D | D |
| 415 | H | $CD_3$ | D | D |

In one embodiment, the compound of Formula B-I is selected from any one of the compounds (Cmpd) set forth in Table 4 above, wherein the stereochemistry at the carbon bearing $Y^{1a}$ and $Y^{1b}$ is (R), or a pharmaceutically acceptable salt thereof, wherein any atom not designated as deuterium in any of the compounds set forth therein is present at its natural isotopic abundance.

In one embodiment, the compound of Formula B-I is selected from any one of the compounds (Cmpd) set forth in Table 4 above, wherein the stereochemistry at the carbon bearing $Y^{1a}$ and $Y^{1b}$ is (S), or a pharmaceutically acceptable salt thereof, wherein any atom not designated as deuterium in any of the compounds set forth therein is present at its natural isotopic abundance.

In one embodiment of the present invention, the compound of Formula B is a compound of Formula C:

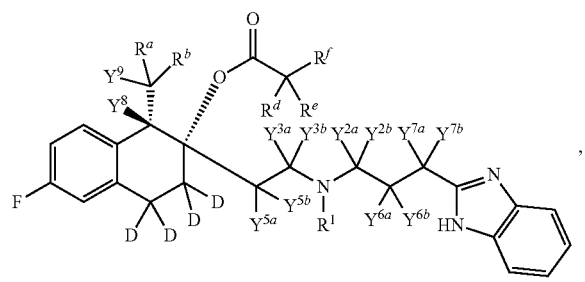

Formula (C)

or a pharmaceutically acceptable salt thereof, wherein
$R^d$ and $R^e$ are each independently hydrogen or deuterium; or $R^d$ and $R^e$ taken together with the carbon to which they are connected form a 3-membered carbocyclic ring that is optionally substituted with deuterium;
provided that if $R^d$ and $R^e$ are each independently hydrogen or deuterium, then $R^f$ is $OR^c$ wherein $R^c$ is selected from —$CH_3$ and —$CD_3$;
and provided that if $R^d$ and $R^e$ taken together with the carbon to which they are connected form a 3-membered carbocyclic ring, then $R^f$ is hydrogen or deuterium;
$Y^{3a}$ and $Y^{3b}$ are each independently selected from hydrogen and deuterium;
$Y^{5a}$ and $Y^{5b}$ are each independently selected from hydrogen and deuterium;
$Y^8$ is selected from hydrogen and deuterium;
$Y^9$ is selected from hydrogen and deuterium;
$R^1$ is selected from —$CH_3$ and —$CD_3$; and
each of $Y^{2a}$, $Y^{2b}$, $Y^{6a}$, $Y^{6b}$, $Y^{7a}$ and $Y^{7b}$ is the same and is either hydrogen or deuterium.

In one embodiment, the compound of Formula C is selected from any one of the compounds (Cmpd) set forth in Table 5a below, or a pharmaceutically acceptable salt thereof, wherein any atom not designated as deuterium in any of the compounds set forth therein is present at its natural isotopic abundance:

TABLE 5a

Examples of Compounds of Formula C wherein $Y^8$, $Y^9$ are each hydrogen; $R^a$ and $R^b$ are each —$CH_3$ and each of $Y^{3a}$, $Y^{3b}$, $Y^{5a}$, and $Y^{5b}$ is hydrogen

| Cmpd # | $R^1$ | Each of $Y^{2a}$, $Y^{2b}$, $Y^{6a}$, $Y^{6b}$, $Y^{7a}$ and $Y^{7b}$ | $R^d$  $R^e$ $R^f$ |
|---|---|---|---|
| 701a | $CH_3$ | D | $CH_2OCH_3$ |
| 702a | $CD_3$ | H | $CH_2OCH_3$ |
| 703a | $CD_3$ | D | $CH_2OCH_3$ |

TABLE 5a-continued

Examples of Compounds of Formula C wherein $Y^8$, $Y^9$ are each hydrogen; $R^a$ and $R^b$ are each —$CH_3$ and each of $Y^{3a}$, $Y^{3b}$, $Y^{5a}$, and $Y^{5b}$ is hydrogen

| Cmpd # | $R^1$ | Each of $Y^{2a}$, $Y^{2b}$, $Y^{6a}$, $Y^{6b}$, $Y^{7a}$ and $Y^{7b}$ | $R^d$  $R^e$ $R^f$ |
|---|---|---|---|
| 704a | $CH_3$ | H | cyclopropyl |
| 705a | $CH_3$ | D | cyclopropyl |
| 706a | $CD_3$ | H | cyclopropyl |
| 707a | $CD_3$ | D | cyclopropyl |

In one embodiment, the compound of Formula C is selected from any one of the compounds (Cmpd) set forth in Table 5b below, or a pharmaceutically acceptable salt thereof, wherein any atom not designated as deuterium in any of the compounds set forth therein is present at its natural isotopic abundance:

TABLE 5b

Examples of Compounds of Formula C wherein $Y^8$, $Y^9$ are each hydrogen; $R^a$ and $R^b$ are each —$CH_3$ and each of $Y^{3a}$, $Y^{3b}$, $Y^{5a}$, and $Y^{5b}$ is deuterium

| Cmpd # | $R^1$ | Each of $Y^{2a}$, $Y^{2b}$, $Y^{6a}$, $Y^{6b}$, $Y^{7a}$ and $Y^{7b}$ | $R^d$  $R^e$ $R^f$ |
|---|---|---|---|
| 700b | $CH_3$ | H | $CH_2OCH_3$ |
| 701b | $CH_3$ | D | $CH_2OCH_3$ |
| 702b | $CD_3$ | H | $CH_2OCH_3$ |
| 703b | $CD_3$ | D | $CH_2OCH_3$ |
| 704b | $CH_3$ | H | cyclopropyl |
| 705b | $CH_3$ | D | cyclopropyl |
| 706b | $CD_3$ | H | cyclopropyl |
| 707 | $CD_3$ | D | cyclopropyl |

In one embodiment, the compound of Formula B is selected from any one of the compounds (Cmpd) set forth in Table 6a below, or a pharmaceutically acceptable salt thereof, wherein any atom not designated as deuterium in any of the compounds set forth therein is present at its natural isotopic abundance:

TABLE 6a

Examples of Compounds of Formula B wherein $R^a$ and $R^b$ are each —$CH_3$, each $Y^1$ is fluorine; $Y^8$ is hydrogen; and $Y^9$ is hydrogen

| Cmpd # | Each of $Y^{2a}$, $Y^{2b}$, $Y^{3a}$, $Y^{3b}$, $Y^{4a}$, $Y^{4b}$, $Y^{5a}$, $Y^{5b}$, $Y^{6a}$, $Y^{6b}$, $Y^{7a}$, and $Y^{7b}$, | $R^1$ | $R^d$  $R^e$ $R^f$ |
|---|---|---|---|
| 800a | H | $CH_3$ | $CH_2OCH_3$ |
| 801a | H | $CD_3$ | $CH_2OCH_3$ |
| 802a | D | $CH_3$ | $CH_2OCH_3$ |
| 803a | D | $CD_3$ | $CH_2OCH_3$ |
| 804a | H | $CH_3$ | cyclopropyl |
| 805a | H | $CD_3$ | cyclopropyl |
| 806a | D | $CH_3$ | cyclopropyl |
| 807a | D | $CD_3$ | cyclopropyl |

In one embodiment, the compound of Formula B is selected from any one of the compounds (Cmpd) set forth in Table 6b below, or a pharmaceutically acceptable salt thereof, wherein any atom not designated as deuterium in any of the compounds set forth therein is present at its natural isotopic abundance:

TABLE 6b

Examples of Compounds of Formula B wherein $R^a$ and $R^b$ are each —$CH_3$, each $Y^1$ is deuterium; $Y^8$ is hydrogen; and $Y^9$ is hydrogen

| Cmpd # | Each of $Y^{2a}$, $Y^{2b}$, $Y^{3a}$, $Y^{3b}$, $Y^{4a}$, $Y^{4b}$, $Y^{5a}$, $Y^{5b}$, $Y^{6a}$, $Y^{6b}$, $Y^{7a}$, and $Y^{7b}$, | $R^1$ |  $R^d$  $R^e$  $R^f$ |
|---|---|---|---|
| 800b | H | $CH_3$ | $CH_2OCH_3$ |
| 801b | H | $CD_3$ | $CH_2OCH_3$ |
| 802b | D | $CH_3$ | $CH_2OCH_3$ |
| 803b | D | $CD_3$ | $CH_2OCH_3$ |
| 804b | H | $CH_3$ | cyclopropyl |
| 805b | H | $CD_3$ | cyclopropyl |
| 806b | D | $CH_3$ | cyclopropyl |
| 807b | D | $CD_3$ | cyclopropyl |

In one embodiment, the compound of Formula B is selected from any one of the compounds (Cmpd) set forth in Table 6c below, or a pharmaceutically acceptable salt thereof, wherein any atom not designated as deuterium in any of the compounds set forth therein is present at its natural isotopic abundance:

TABLE 6c

Examples of Compounds of Formula B wherein $R^a$ and $R^b$ are each —$CH_3$, each $Y^1$ is hydrogen; $Y^8$ is hydrogen; and $Y^9$ is hydrogen

| Cmpd # | Each of $Y^{2a}$, $Y^{2b}$, $Y^{3a}$, $Y^{3b}$, $Y^{4a}$, $Y^{4b}$, $Y^{5a}$, $Y^{5b}$, $Y^{6a}$, $Y^{6b}$, $Y^{7a}$, and $Y^{7b}$, | $R^1$ | $R^d$  $R^e$  $R^f$ |
|---|---|---|---|
| 801c | H | $CD_3$ | $CH_2OCH_3$ |
| 802c | D | $CH_3$ | $CH_2OCH_3$ |
| 803c | D | $CD_3$ | $CH_2OCH_3$ |
| 805c | H | $CD_3$ | cyclopropyl |
| 806c | D | $CH_3$ | cyclopropyl |
| 807c | D | $CD_3$ | cyclopropyl |

In one embodiment of the present invention, the compound of Formula B is a compound of Formula E:

Formula (E)

or a pharmaceutically acceptable salt thereof, wherein
$R^d$ and $R^e$ are each independently hydrogen or deuterium; or $R^d$ and $R^e$ taken together with the carbon to which they are connected form a 3-membered carbocyclic ring that is optionally substituted with deuterium;
provided that if $R^d$ and $R^e$ are each independently hydrogen or deuterium, then $R^f$ is $OR^c$ wherein $R^c$ is selected from —$CH_3$ and —$CD_3$;
and provided that if $R^d$ and $R^e$ taken together with the carbon to which they are connected form a 3-membered carbocyclic ring, then $R^f$ is hydrogen or deuterium;
$Y^{3a}$ and $Y^{3b}$ are each independently selected from hydrogen and deuterium;
$Y^{5a}$ and $Y^{5b}$ are each independently selected from hydrogen and deuterium;
$Y^8$ is selected from hydrogen and deuterium;
$Y^9$ is selected from hydrogen and deuterium;
$R^1$ is selected from —$CH_3$ and —$CD_3$; and
each of $Y^{2a}$, $Y^{2b}$, $Y^{6a}$, $Y^{6b}$, $Y^{7a}$ and $Y^{7b}$ is the same and is either hydrogen or deuterium.

In one embodiment the invention is directed to Compound 622 or a pharmaceutically acceptable salt thereof, wherein any atom not designated as deuterium in any of the compounds set forth therein is present at its natural isotopic abundance:

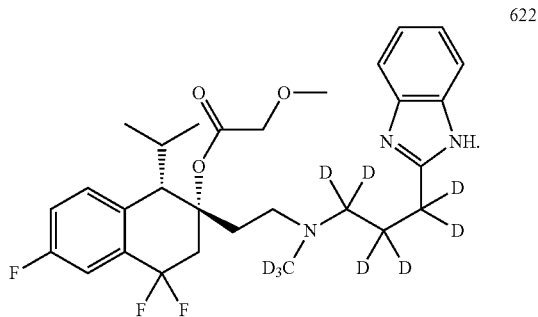 [SMILES: [2H]C([2H])([2H])N(CC[C@@]1(OC(=O)COC)CC(F)(F)c2cc(F)ccc2[C@@H]1C(C)C)C([2H])([2H])C([2H])([2H])C([2H])([2H])c1nc2ccccc2[nH]1]

622

In one embodiment the invention is directed to Compound 808a or a pharmaceutically acceptable salt thereof, wherein any atom not designated as deuterium in any of the compounds set forth therein is present at its natural isotopic abundance:

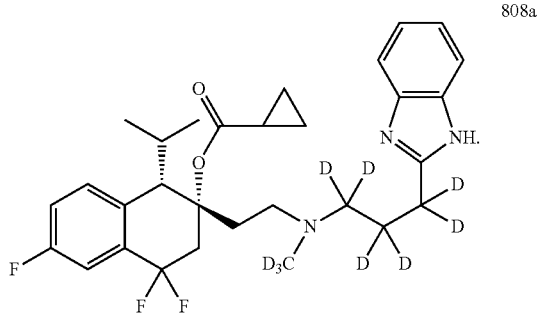 [SMILES: [2H]C([2H])([2H])N(CC[C@@]1(OC(=O)C2CC2)CC(F)(F)c2cc(F)ccc2[C@@H]1C(C)C)C([2H])([2H])C([2H])([2H])C([2H])([2H])c1nc2ccccc2[nH]1]

808a

In one embodiment the invention is directed to compounds of Formula IIa-d or salts thereof:

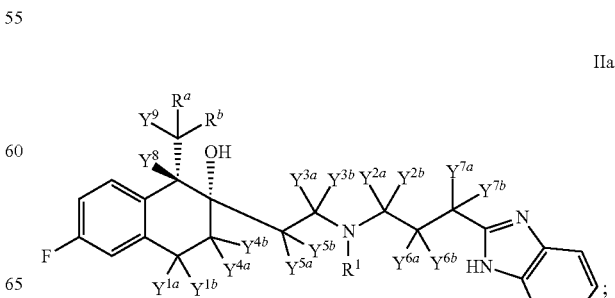

IIa

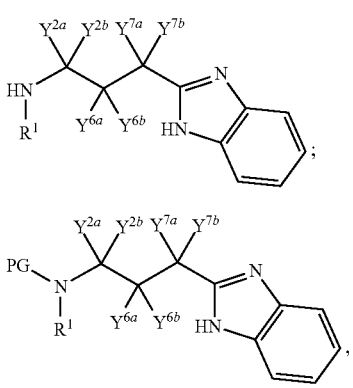

wherein PG in IIc is a protecting group such as (i) ($C_6$-$C_{10}$ aryl)$CH_2$—, such as benzyl or (ii) $C_1$-$C_6$ alkyl-OC(O)—, such as Boc (t-butoxycarbonyl); and

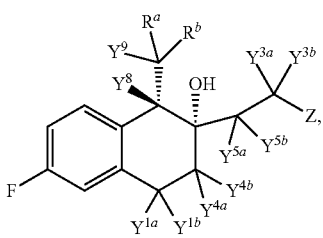

wherein Z in IId is a leaving group, such as halogen; ($C_1$-$C_6$ alkyl)-$SO_3$ wherein the $C_1$-$C_6$ alkyl is optionally substituted with halogen; and ($C_6$-$C_{10}$ aryl)-$SO_3$ wherein the $C_6$-$C_{10}$ aryl is optionally substituted with alkyl, halogen, or a combination thereof, provided that (a) in IIa, IIb, and IIc, when each Y is hydrogen, then $R^1$ comprises at least one deuterium; and (b) in IId, at least one Y is deuterium. In one embodiment, any atom not designated as deuterium in any of IIa-IId is present at its natural isotopic abundance.

The synthesis of compounds of Formula B, Formula A, Formula I, Formula B-I, Formula C and Formula E may be readily achieved by synthetic chemists of ordinary skill by reference to the Exemplary Synthesis and Examples disclosed herein. Relevant procedures analogous to those of use for the preparation of compounds of Formula B, Formula A, Formula I, Formula B-I, Formula C and Formula E and intermediates thereof are disclosed, for instance in U.S. Pat. No. 4,808,605, U.S. Pat. No. 5,808,088 and PCT Publication No. WO 98/49148.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

Compounds of Formula B, Formula A, Formula I, Formula B-I, Formula C and Formula E may be conveniently prepared in a manner analogous to that described in U.S. Pat. No. 4,808,605 (the "'605 patent") by replacing the reagents and/or starting materials described in the schemes and the examples in the '605 patent with suitable deuterated counterparts to obtain derivatives of mibefradil having the deuteration patterns disclosed herein. For example, the deuterated counterparts of the reagents and/or starting materials described in the schemes and examples of the '605 patent may be commercially available deuterated compounds. The schemes of the '605 patent, shown on column 7, line 7—column 12, line 57, and the examples of the '605 patent, shown on column 16, line 1—column 40, line 51, are incorporated by reference herein. Compounds of Formula B, Formula A, Formula I, Formula B-I, Formula C and Formula E may also be conveniently prepared in a manner analogous to the one described in U.S. Pat. No. 5,808,088 (the "'088 patent") by replacing the reagents and/or starting materials described in the schemes and the examples in the '088 patent with suitable deuterated counterparts to obtain derivatives of mibefradil having the deuteration patterns disclosed herein. For example, the deuterated counterparts of the reagents and/or starting materials described in the schemes and examples of the '088 patent may be commercially available deuterated compounds. The disclosure of the '088 patent from col. 1, line 65 to col. 3, line 2; column 3, lines 3—column 6, line 60, and the example of the '088 patent, shown on column 6, line 61—column 9, line 57, are incorporated by reference herein. Compounds of Formula B, Formula A, Formula I, Formula B-I, Formula C and Formula E may also be conveniently prepared in a manner analogous to the one described in PCT Publication No. WO 98/49148 (the "'148 patent") by replacing the reagents and/or starting materials described in the schemes and the examples in the '148 patent with suitable deuterated counterparts to obtain derivatives of mibefradil having the deuteration patterns disclosed herein. For example, the deuterated counterparts of the reagents and/or starting materials described in the schemes and examples of the '148 patent may be commercially available deuterated compounds. The disclosure of the '148 patent from page 2, line 4—page 4, line 7; page 4, line 10—page 9, line 35, and the example of the '148 patent, shown on page 10, line 1—page 15—line 26, are incorporated by reference herein. Compounds of Formula B, Formula A, Formula I, Formula B-I, Formula C and Formula E may also be conveniently prepared in a manner analogous to the one described in Casas et al., *Drugs of the Future* 1997, Vol. 22, p. 1091-1102 by replacing the reagents and/or starting materials described in the schemes and the examples with suitable deuterated counterparts to obtain derivatives of mibefradil having the deuteration patterns disclosed herein. For example, the deuterated counterparts of the reagents and/or starting materials described in the schemes and examples of Casas et al. may be commercially available deuterated compounds. The disclosure of Casas et al. on page 1091 and on page 1092 (Scheme 1) is incorporated by reference herein. Such approaches are not intended to be limiting.

Scheme 1 below outlines a general route for preparing compounds of Formula B, Formula A, Formula I, Formula B-I, Formula C and Formula E.

Scheme 1: General Route to Compounds of Formula B.
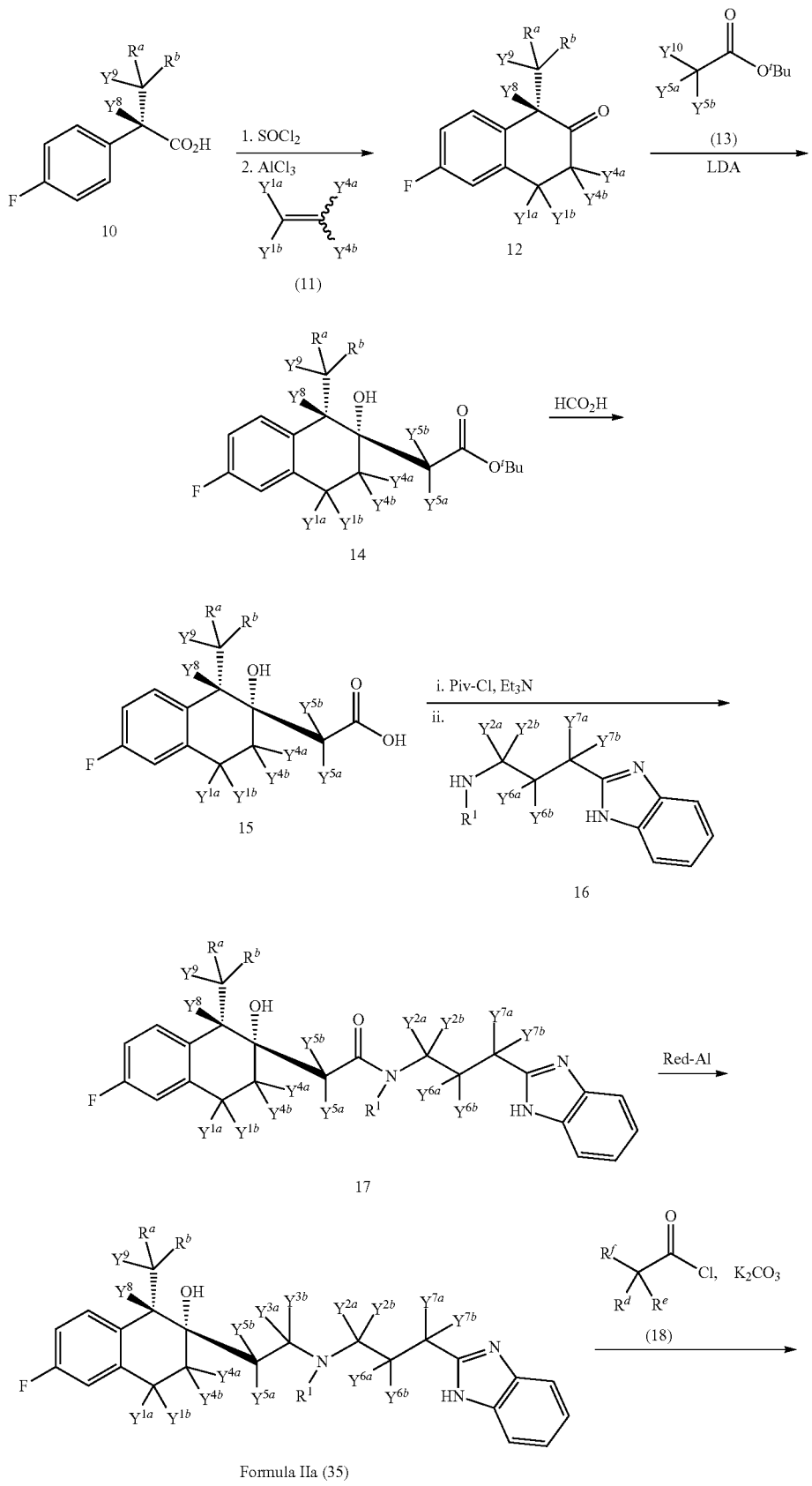

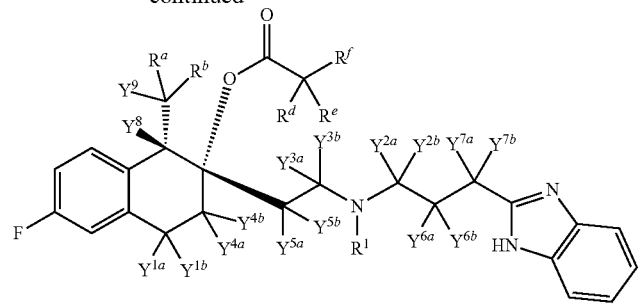

Formula B

Scheme 1 depicts a general route to compounds of Formula B following the general methods of Hengartner, U. et al., U.S. Pat. No. 4,680,310; and the '148 patent. Deuterated carboxylic acid 10 may be converted to the acid chloride and coupled with deuterated ethylene 11 using the procedure described by Hengartner, U. et al., U.S. Pat. No. 4,680,310 to afford ketone 12. The remaining steps can be performed under conditions previously described by the '148 patent. Condensation of 12 with the lithium enolate of deuterated ester 13 (wherein $Y^{10}$, $Y^{5a}$, and $Y^{5b}$ are the same and are either hydrogen or deuterium) affords alcohol 14. Acidic cleavage of the tert-butyl ester with formic acid, formation of the mixed anhydride with pivaloyl chloride and coupling with deuterated amine 16 (compounds of Formula IIb) affords amide 17. Reductive removal of the carbonyl group with Red-Al followed by coupling of the alcohol moiety with acid chloride 18 affords compounds of Formula B. One skilled in the art will appreciate that deuterated solvents and reagents may be substituted, where appropriate, to afford compounds of Formula B bearing different patterns of deuterium substitution.

As an example, the pathway shown in Scheme I may be useful to obtain compounds of Formula A wherein each $Y^1$ and each $Y^4$ is deuterium.

The following intermediates that may be used in Scheme 1 above are commercially available:

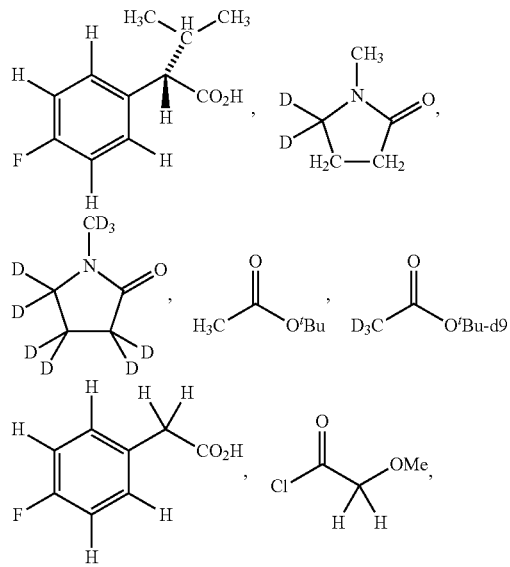

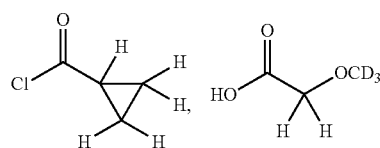

Additional useful intermediates may be prepared as outlined in the schemes below. One skilled in the art will appreciate that deuterated solvents and reagents may be substituted, where appropriate, to afford intermediates bearing different patterns of deuterium substitution.

Scheme 2. Preparation of Intermediate 16a, wherein $R^1$ is $CD_3$ and $Y^{2a}$, $Y^{2b}$, $Y^{6a}$, $Y^{6b}$, $Y^{7a}$ and $Y^{7b}$ are each deuterium.

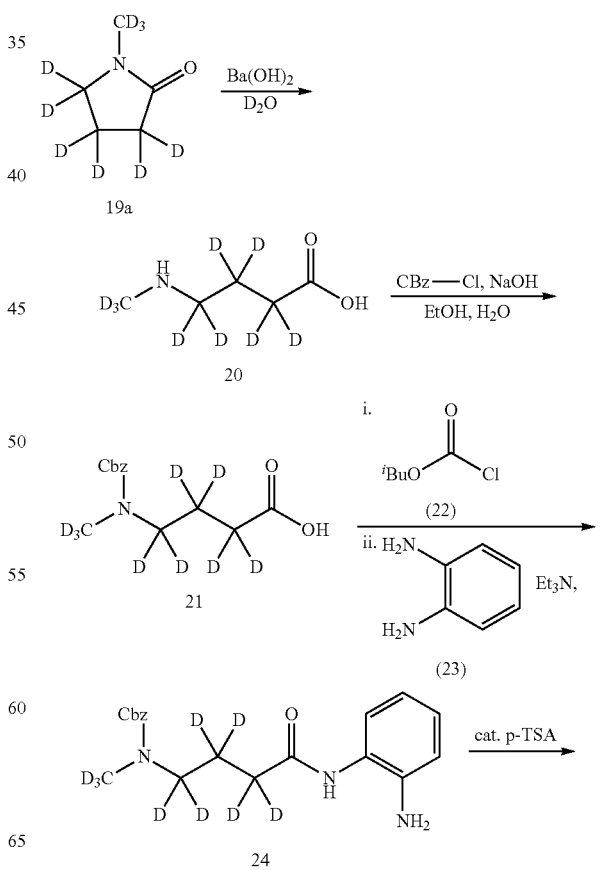

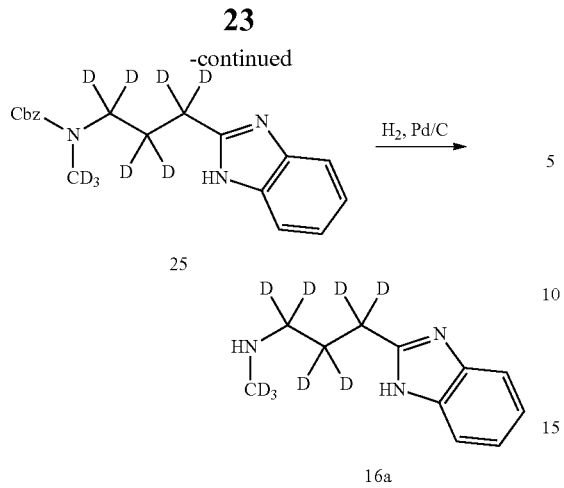

26  19b

Intermediate 16a may be prepared from pyrrolidinone 19a as shown in Scheme 2 above. Following the protocol described in Galakatos, N. G. et al., J. Org. Chem. 1985, 50, 1302-1304, the pyrrolidinone ring of 19a may be opened with Ba(OH)$_2$ and the resulting free amine protected with CBzCl to afford carbamate 21. The remaining steps can be performed under conditions previously described in Shin, K. J. et al., Biorg. Med. Chem. Lett. 2008, 18, 4424-4427. The carboxylic acid moiety of 21 may be activated with isobutyl chloroformate and then coupled with benzene-1,2-diamine to afford amide 24. Cyclization to form benzimidazole 25 may be effected under acidic conditions, following which hydrogenolysis of the carbamate with Pd/C affords intermediate 16a.

Scheme 3. Preparation of Intermediate 19b, wherein R$^1$ is CD$_3$ and Y$^{2a}$ and Y$^{2b}$ are each deuterium.

Intermediate 19b may be prepared as shown in Scheme 3 above according to the method of Djerassi, C. et al., J. Am. Chem. Soc. 1964, 86, 5536-5541. Reduction of a single carbonyl group of commercially-available succinimide 26 with LiAlD$_4$ followed by alkylation of the nitrogen atom with CD$_3$I affords pyrrolidinone 19b. 19b may be then converted to 16b in accordance with the procedure of Scheme 2 used to convert 19a to 16a.

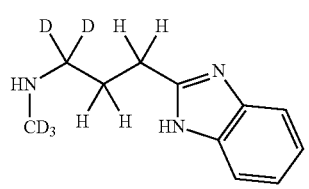

16b

Similarly, 16c and 16d may be prepared using appropriately deuterated solvents and reagents:

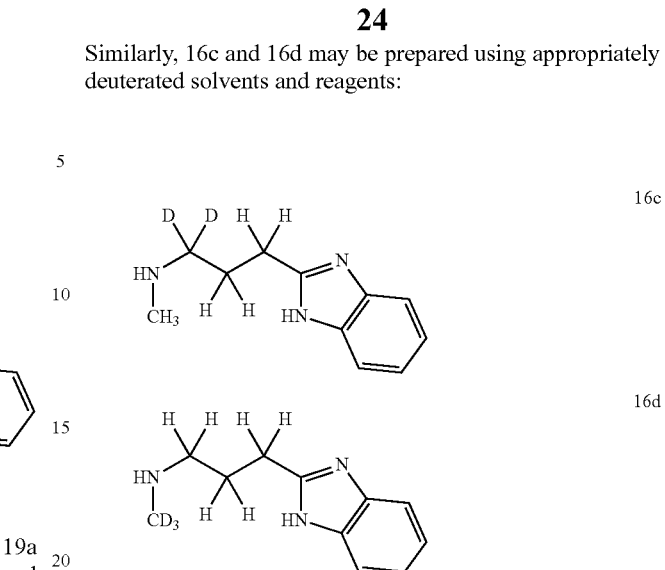

Scheme 4a. Preparation of Intermediate 12b wherein Y$^{1a}$ and Y$^{1b}$ are each fluorine, Y$^{4a}$, Y$^{4b}$, Y$^8$ and Y$^9$ are each hydrogen, and R$^a$ and R$^b$ are each CH$_3$.

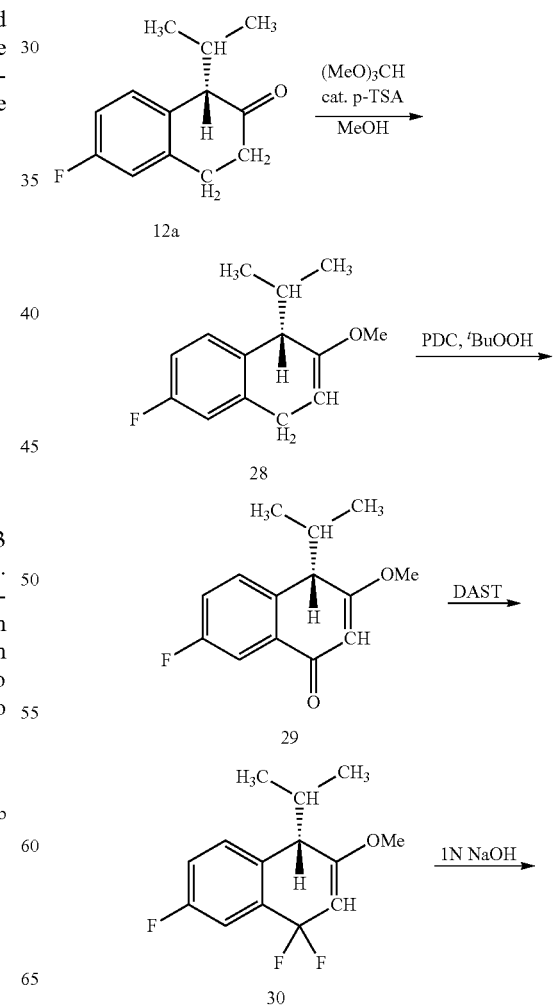

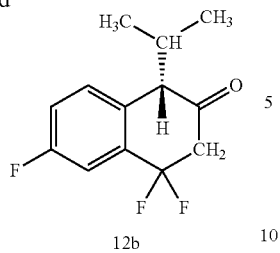

12b

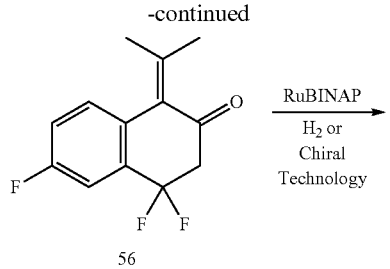

56

The preparation of fluorinated intermediate 12b is shown in Scheme 4a above. Following conditions previously described in Krueger, A. C. et al., Biorg. Med. Chem. Lett. 2007, 17, 2289-2292, ketone 12a (prepared as in Scheme 1 above from 2-(4-fluorophenyl)-3-methyl-butyric acid and ethylene) is converted to enone 29 via conversion to enol ether 28 followed by palladium dichromate-mediated oxidation to 29. Treatment of 29 with diethylaminosulfur trifluoride (DAST) affords 30. Basic hydrolysis of the enol ether moiety affords 12b. 12b may be then converted to a Compound of Formula B wherein each $Y^1$ is fluorine in accordance with Scheme 1 above.

Scheme 4b. Alternative preparation of intermediate 12b

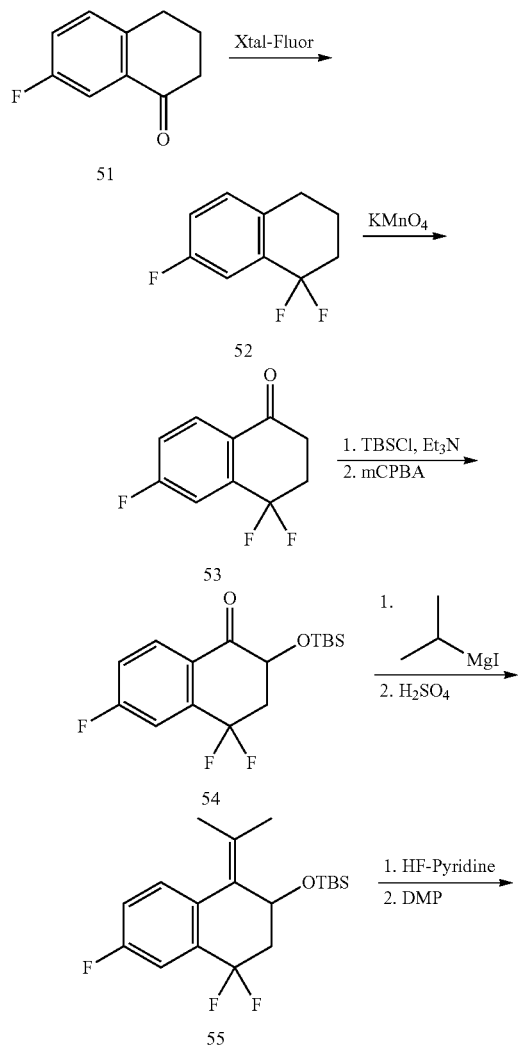

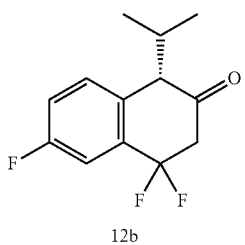

12b

1. WO1996026181
2. J. Am. Chem. Soc., 107(15), 4577-9; 1985

An alternative preparation of fluorinated intermediate 12b is shown in Scheme 4b above. 51 is treated with XtalFluor, such as XtalFluor-E or XtalFluor M to afford 52. Other fluorinating agents that may be used to afford 52 are within the purview of one skilled in the art. Oxidation of 52 with $KMnO_4$ in a manner analogous to the one described in WO1996/26181 affords 53. Silylation of 53 followed by oxidation with mCPBA in a manner analogous to that of *J. Am. Chem. Soc.,* 107(15), 4577-9; 1985 provides 54, which on treatment with isopropyl magnesium iodide is converted to 55. Treatment of 55 with HF-pyridine gives 56, which is then treated with hydrogen in the presence of Ru/BINAP to yield 57. Other chiral catalysts may be used to afford 12b.

Scheme 5. Preparation of Intermediate (S)-12c wherein $Y^8$ and $Y^9$ are each deuterium, and $R^a$ and $R^b$ are each $CD_3$.

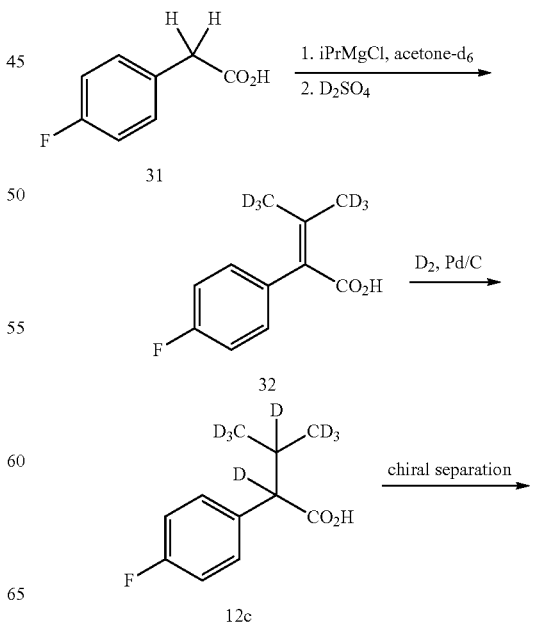

12c

-continued

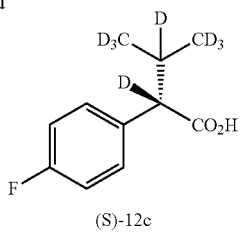

(S)-12c

The preparation of deuterated intermediate (S)-12c is shown in Scheme 5 above. Following a protocol previously described in Scalone, M. et al., Tetrahedron Asymm. 1997, 8, 3617-3623, i-PrMgCl-mediated aldol addition of commercially-available 31 to acetone-$d_6$ followed by acid-catalyzed dehydration of the aldol product affords crotonic acid 32. Palladium-mediated deuterogenation of the alkene moiety affords 12c. Chiral separation of the enantiomers of 12c affords (S)-12c.

Scheme 6. Preparation of intermediate 18a wherein $R^d$ and $R^e$ are each deuterium and $R^f$ is $CD_3$.

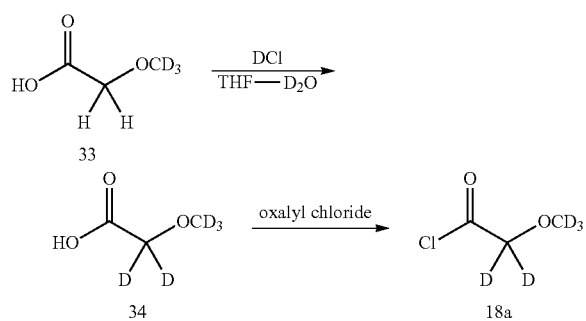

A possible route for the preparation of deuterated intermediate 18a is shown in Scheme 6 above. Acid-catalyzed hydrogen-deuterium exchange at the α-carbon affords acid 34. Treatment of 34 with oxalyl chloride affords acid chloride 18a.

Additional methods of synthesizing compounds of Formula B, Formula A, Formula I, Formula B-I, Formula C and Formula E and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene, T W et al., *Protective Groups in Organic Synthesis*, 3$^{rd}$ Ed., John Wiley and Sons (1999); Fieser, L et al., *Fieser and Fieser's Reagents for Organic Synthesis*, John Wiley and Sons (1994); and Paquette, L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pyrogen-free pharmaceutical compositions comprising an effective amount of a compound of Formula B, Formula A, Formula I, Formula B-I, Formula C or Formula E (e.g., including any of the formulae herein), or a pharmaceutically acceptable salt of said compound; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the subject, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as mibefradil. Such agents include beta blockers, aldose reductase inhibitors, NSAIDs, $5HT_{1D}$ agonists, dopamine $D_2$ receptor antagonists, secale alkaloids, a second calcium channel blocker and neurokinin antagonists.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat the target disorder.

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

In one embodiment, an effective amount of a compound of this invention can range from 10 mg to 200 mg per day, from 50-100 mg/day, or from 20-50 mg/day.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician. For example, guidance for selecting an effective dose can be determined by reference to the prescribing information for mibefradil.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of modulating the activity of calcium channel in a cell, comprising contacting a cell with one or more compounds of Formula B, Formula A, Formula I, Formula B-I, Formula C or Formula E herein or pharmaceutically acceptable salts thereof.

According to another embodiment, the invention provides a method of treating a disease that is beneficially treated by mibefradil in a subject in need thereof, comprising the step of administering to the subject an effective amount of a compound or a composition of this invention. Such diseases include, but are not limited to angina pectoris, ischemia, arrhythmias, congestive heart failure, high blood pressure, cardiac insufficiency, pain, visceral pain and diabetic complications (such as diabetic neuropathy, diabetic nephropathy, diabetic retinopathy, myocardial infarction, cataracts and diabetic cardiomyopathy).

In one particular embodiment, the method of this invention is used to treat a disease or condition selected from hypertension and angina pectoris in a subject in need thereof.

In another particular embodiment, the method of this invention is used to treat congestive heart failure in a subject in need thereof.

Identifying a subject in need of such treatment can be in the judgment of a subject or a health care professional and can be subjective (e.g. opinion) or objective (e.g. measurable by a test or diagnostic method).

In another embodiment, any of the above methods of treatment comprises the further step of co-administering to the subject in need thereof one or more second therapeutic agents. The choice of second therapeutic agent may be made from any second therapeutic agent known to be useful for co-administration with mibefradil. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In particular, the invention provides a method of treating a disease or condition selected from arrhythmias, hypertension and angina pectoris in a subject comprising the step of co-administering to the subject in need thereof a compound of Formula B, Formula A, Formula I, Formula B-I, Formula C or Formula E or a pharmaceutically acceptable salt of said compound, and a beta blocker.

In another embodiment, the invention provides a method of treating a diabetic complication in a subject comprising the step of co-administering to the subject in need thereof a compound of Formula B, Formula A, Formula I, Formula B-I, Formula C or Formula E or a pharmaceutically acceptable salt of said compound, and an aldose reductase inhibitor.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula B, Formula A, Formula I, Formula B-I, Formula C or Formula E or a pharmaceutically acceptable salt of the compound, alone or together with one or more of the above-described second therapeutic agents in the manufacture of a medicament, either as a single composition or as separate dosage forms, for treatment or prevention in a subject of a disease, disorder or symptom set forth above. Another aspect of the invention is a compound of Formula B, Formula A, Formula I, Formula B-I, Formula C or Formula E or a pharmaceutically acceptable salt of the compound, for use in the treatment or prevention in a subject of a disease, disorder or symptom thereof delineated herein.

EXAMPLES

In the examples below, any atom not designated as deuterium is present at its natural isotopic abundance.

Example 1

Preparation of 2-((1S,2S)-3,3,4,4-Tetradeutero-6-fluoro-2-hydroxy-1-isopropyl-1,2,3,4-tetrahydronaphthalen-2-yl)acetic acid (15b)

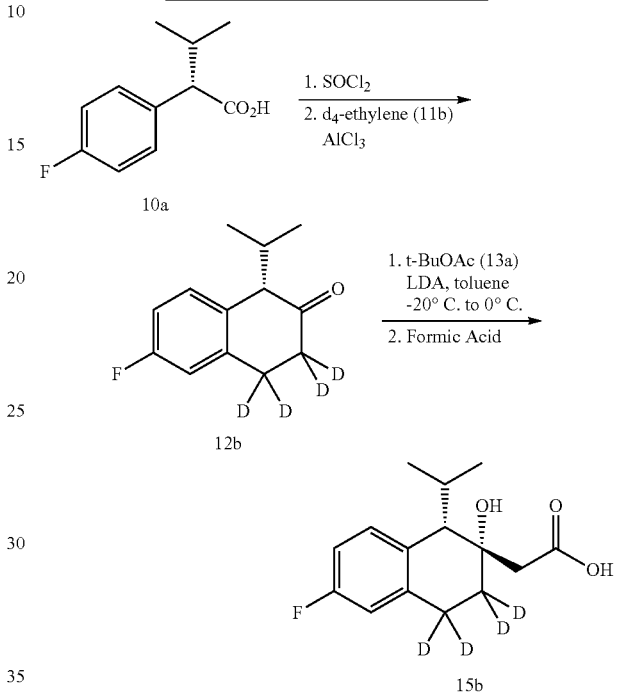

Step 1. (S)-3,3,4,4-Tetradeutero-6-fluoro-1-isopropyl-3,4-dihydronaphthalen-2(1H)-one (S)-2-(4-fluorophenyl)-3-methylbutanoic acid 10a (1.05 g, 5.38 mmol; prepared as describe in Crameri, Y. et al. Tetrahedron: Asymmetry 1997, 8: 3617-3623) was dissolved in benzene (18 mL, 0.3M) and thionyl chloride (0.785 mL, 10.7 mmol) was added by syringe. The reaction was then heated to a gentle reflux under a blanket of nitrogen for four hours. The reaction was concentrated under reduced pressure and an aliquot was removed in order to confirm conversion to the acyl chloride by $^1$H NMR. The acyl chloride was dissolved in dichloromethane (150 mL, 0.04M) and the resulting solution was cooled with an ice bath. The reaction solvent was saturated with $d_4$-ethylene gas (ISOTEC, 98% D) for 30 minutes. Next, aluminum trichloride (2.15 g, 16.1 mmol) was added as a single portion to the reaction and sparging was continued for an additional 30 minutes. The reaction was poured into ice-cold HCl (100 mL, 1M) and stirred for 10 minutes. The aqueous phase was extracted with dichloromethane (3×50 mL). The combined organics were dried over sodium sulfate, filtered, and concentrated to give a yellow oil. Purification with an ISCO flash chromatography instrument using heptanes/ethyl acetate as the eluent (gradient: 0-100%) afforded 12b as a colorless oil (570 mg, 2.97 mmol, 58% yield). $^1$H NMR (400 MHz, CDCl$_3$): δ 7.01 (m, 1H), 6.91 (m, 2H), 3.05 (d, J=8 Hz, 1H), 2.20 (m, 1H), 1.00 (d, J=6.4 Hz, 3H), 0.81 (d, J=6.4 Hz, 1H).

Step 2. 2-((1S,2S)-3,3,4,4-Tetradeutero-6-fluoro-2-hydroxy-1-isopropyl-1,2,3,4-tetrahydronaphthalen-2-yl)acetic acid (15b)

A solution of diisopropylamine (0.906 mL, 6.5 mmol) in toluene (13 mL) was cooled with a dry ice acetone bath to −78° C. Next was added a 1.5M n-butyllithium solution (4.33 mL, 6.5 mmol) by syringe and the resulting solution of LDA was stirred for 10 minutes at −78° C. followed by warming to 0° C. for 30 minutes. The solution was then cooled to −78° C. again and tert-butylacetate (1.05 mL, 7.80 mmol) was added as a neat oil. The reaction was stirred for an additional 30 minutes to afford an approximately 0.5 M solution of tert-butylacetate lithium enolate.

In a separate flask ketone 12b (450 mg, 2.14 mmol) was dissolved in toluene (12 mL, 0.18M) and cooled to −78° C. Then the previously prepared 0.5M enolate solution (9.42 mL, 4.71 mmol) was added to the solution of 12b over 30 minutes by syringe pump. After 1 hour, the reaction was transferred to a cryocool chiller set to −20° C. and stirred under a balloon of nitrogen for 12 hours. The reaction was poured into an ice-cold 1M HCl (100 mL) solution and the mixture was extracted with ethyl acetate. The combined organic solutions were concentrated to give tert-butyl 2-((1S,2S)-3,3,4,4-tetradeutero-6-fluoro-2-hydroxy-1-isopropyl-1,2,3,4-tetrahydronaphthalen-2-yl)acetate (14b) as a colorless oil (0.698 g, 2.14 mmol).

Intermediate 14b (0.698 g, 2.14 mmol) was dissolved in formic acid (1 mL) and stirred at ambient temperature for 4 hours. Water (0.75 mL) was added and the reaction heated to 75° C. for 10 minutes. The reaction was cooled and concentrated with a lypholizer to give intermediate 15b as a white solid (513 mg, 1.90 mmol, 90% yield for the two steps). MS (M−H): 269.16.

Example 2

Preparation of N-(3-(1H-Benzo[d]imidazol-2-yl)propyl)-N-methyl-2-((1S,2S)-3,3,4,4-tetradeutero-6-fluoro-2-hydroxy-1-isopropyl-1,2,3,4-tetrahydronaphthalen-2-yl)acetamide [35b] (Formula IIa, wherein $Y^8=Y^9=Y^{5a/b}=Y^{3a/b}=Y^{2a/b}=Y^{6a/b}=Y^{7a/b}=H$, $Y^{1a/b}=Y^{4a/b}=D$ and $R^a=R^b=R^1=CH_3$)]

Scheme 8. Preparation of Intermediate 35b.

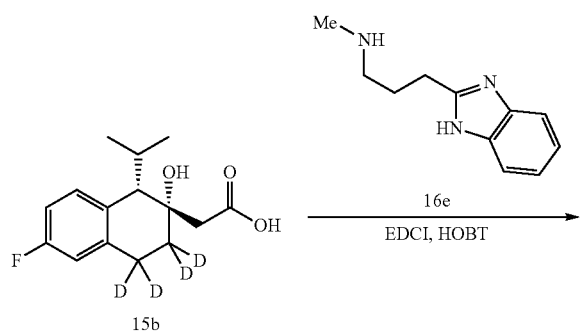

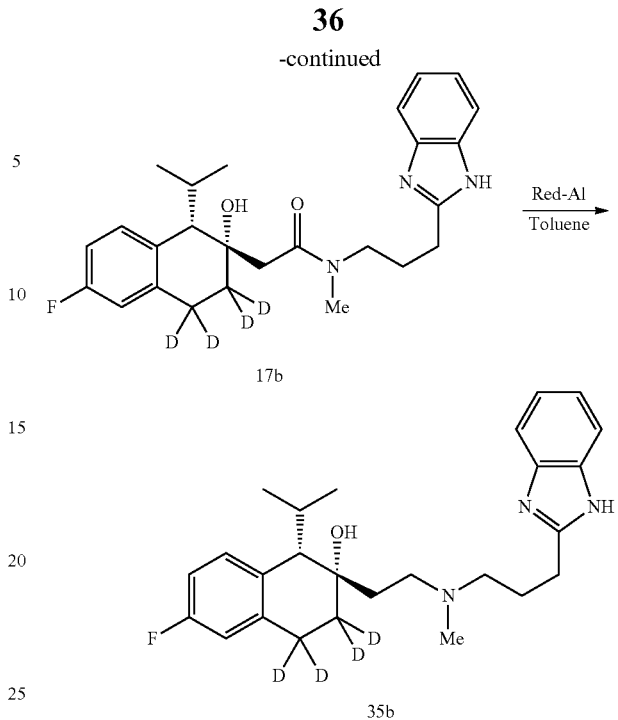

Step 1. N-(3-(1H-Benzo[d]imidazol-2-yl)propyl)-N-methyl-2-((1S,2S)-3,3,4,4-tetradeutero-6-fluoro-2-hydroxy-1-isopropyl-1,2,3,4-tetrahydronaphthalen-2-yl)acetamide (17b)

Intermediate 15b (84 mg, 0.310 mmol.), 3-(1H-benzo[d]imidazol-2-yl)-N-methylpropan-1-amine 16e (148 mg, 0.745 mmol; prepared as described in Lee, H. K. et al. Bioorganic Medicinal Chemistry Letters 2008, 18: 4424-4427) and 1-hydroxybenzotriazole hydrate (HOBT) (78 mg, 0.508 mmol) were dissolved in 2-methyl tetrahydrofuran (2.71 mL). In a separate flask was dissolved N-(3-dimethylaminopropyl)-N'-ethylcarbodiimide hydrochloride (EDCI) (156 mg, 0.812 mmol) in water (2.71 mL). The two solutions were combined and stirred under a nitrogen atmosphere for 12 hours. The reaction was quenched with aqueous ammonium chloride solution and extracted with ethyl acetate. After drying over sodium sulfate, filtration and concentration, the crude material was purified by an ISCO flash chromatography instrument (elution gradient: 0-100% ethyl acetate-heptanes) to yield intermediate 17b as a colorless oil (100 mg, 0.227 mmol, 73% yield). MS [M+H]: 442.3.

Step 2. 1S,2S)-2-(2-((3-(1H-Benzo[d]imidazol-2-yl)propyl)(methyl)amino)ethyl)-3,3,4,4-tetradeutero-6-fluoro-1-isopropyl-1,2,3,4-tetrahydronaphthalen-2-ol (35b)

A solution of sodium bis(2-methoxyethoxy)aluminum hydride (Red-Al) in toluene (0.125 mL, 0.408 mmol) was diluted with additional toluene (0.5 mL) and cooled to 0° C. with an ice bath. A toluene solution (1.0 mL) of 17b (60 mg, 0.136 mmol) was introduced by cannula. After 30 minutes the reaction was allowed to warm to ambient temperature and then heated to 40° C. with an oil bath. The reaction was then stirred under a nitrogen atmosphere at this temperature for 12 hours. It was then cooled, diluted with toluene, and poured into ice cold aqueous sodium hydroxide (1N). The suspension was allowed to warm to ambient temperature. The biphasic mixture was partitioned between water and toluene. The combined organics were dried over sodium sulfate, filtered and concentrated to afford a yellow oil. The crude material was purified with an ISCO flash chromatography instrument, using a 0-20% methanol/dichloromethane/5% ammonia elution gradient, to yield 35b as a colorless oil (40 mg, 0.094 mmol, 69% yield). MS (M+H): 428.4.

Example 3

Preparation of N-(3-(1H-Benzo[d]imidazol-2-yl)propyl)-N-methyl-2-((1S,2S)-3,3,4,4-tetradeutero-6-fluoro-2-hydroxy-1-isopropyl-1,2,3,4-tetrahydronaphthalen-2-yl)acetamide [35c (Formula IIa, wherein $Y^8=Y^9=Y^{5a/b}=Y^{3a/b}=H$, $Y^{1a/b}=Y^{4a/b}=Y^{2a/b}=Y^{6a/b}=Y^{7a/b}=D$, $R^1=CD_3$, and $R^a=R^b=CH_3$)]

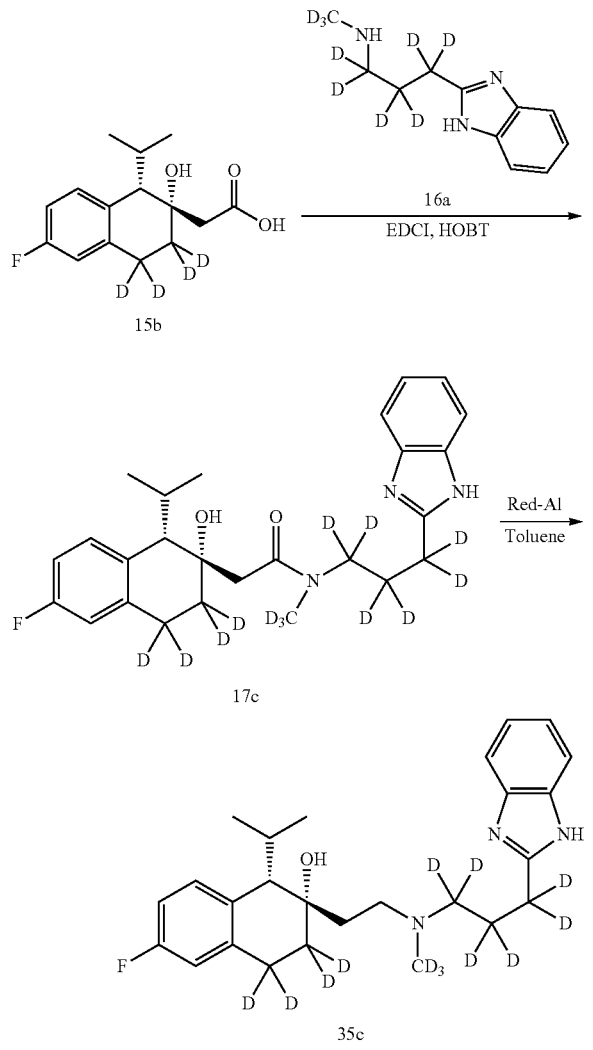

Step 1. N-(3-(1H-Benzo[d]imidazol-2-yl)-1,1,2,2,3,3-hexadeuteropropyl)-2-((1S,2S)-3,3,4,4-tetradeutero-6-fluoro-2-hydroxy-1-isopropyl-1,2,3,4tetrahydronaphthalen-2-yl)-N-(trideuteromethyl)acetamide (17c)

17c was prepared using the procedure for 17b above (Example 2, Step 1) from the union of 15b (162 mg, 0.597 mmol) and amine 16a (130 mg, 0.657 mmol; prepared as described in Example 8 below) to provide 17c as a colorless oil (140 mg, 0.311 mmol, 52% yield). MS (M+H): 451.4.

Step 2. (1S,2S)-2-(2-((3-(1H-Benzo[d]imidazol-2-yl)-1,1,2,2,3,3-hexadeuteropropyl)(trideuteromethyl)amino)-ethyl)-3,3,4,4-tetradeutero-6-fluoro-1-isopropyl-1,2,3,4-tetrahydronaphthalen-2-ol (35c)

35c was prepared, using the procedure for 35b above (Example 2, Step 2), from the treatment of 17c (140 mg, 0.311 mmol) with Red-Al solution (0.285 mL, 0.933 mmol) to give 35c as a colorless oil (95 mg, 0.218 mmol, 70% yield). MS (M+H): 437.4.

Example 4

Synthesis of (1S,2S)-2-(2-(3-(1H-Benzo[d]imidazol-2-yl)propyl)(methyl)amino)ethyl)-3,3,4,4-tetradeutero-6-fluoro-1-isopropyl-1,2,3,4-tetrahydronaphthalen-2-yl 2-methoxyacetate (Compound 500)

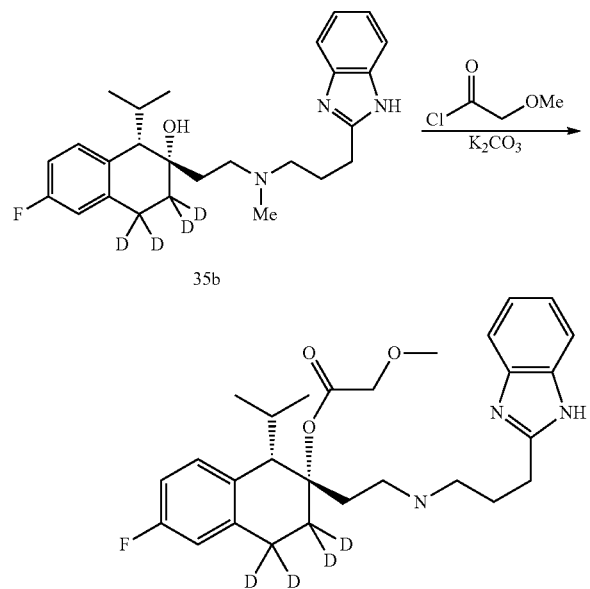

(1S,2S)-2-(2-((3-(1H-Benzo[d]imidazol-2-yl)propyl)(methyl)amino)ethyl)-3,3,4,4-tetradeutero-6-fluoro-1-isopropyl-1,2,3,4-tetrahydronaphthalen-2-yl 2-methoxyacetate (Compound 500)

35b (20 mg, 0.046 mmol) was dissolved in toluene (1 mL). Potassium carbonate (26 mg, 0.184 mmol) and methoxyacetyl chloride (0.015 mL, 0.150 mmol) were added and stirred under a nitrogen atmosphere. Upon completion, the reaction was diluted with ethyl acetate and washed with aqueous sodium hydroxide (1N). The combined organic solutions were dried over sodium sulfate, filtered and concentrated to give an oil which was purified on silica gel to give Compound 500 as a colorless oil (16 mg, 0.032 mmol, 70% yield). ¹H NMR (400 MHz, CDCl₃) δ: 7.44 (m, 2H), 7.20 (m, 2H), 6.91 (m, 1H), 6.86 (m, 1H), 6.72 (dd, J=9.6, 2.8 Hz, 1H), 4.04 (d, J=3.7 Hz, 2H), 3.46 (s, 3H), 3.32 (brs, 1H), 3.10 (m, 2H), 2.89 (m, 1H), 2.70 (m, 2H), 2.43 (s, 3H), 2.13-1.91 (m, 4H), 1.05 (d, J=7.2 Hz, 3H), 0.42 (d, J=7.2 Hz, 3H). MS (M+H): 500.4.

Example 5

Synthesis of (1S,2S)-2-(2-((3-(1H-Benzo[d]imidazol-2-yl)-1,1,2,2,3,3-hexadeuteropropyl)(trideuteromethyl)-amino)ethyl)-3,3,4,4-tetradeutero-6-fluoro-1-isopropyl-1,2,3,4-tetrahydronaphthalen-2-yl 2-methoxyacetate (Compound 703a)

Scheme 11. Synthesis of Compound 703a

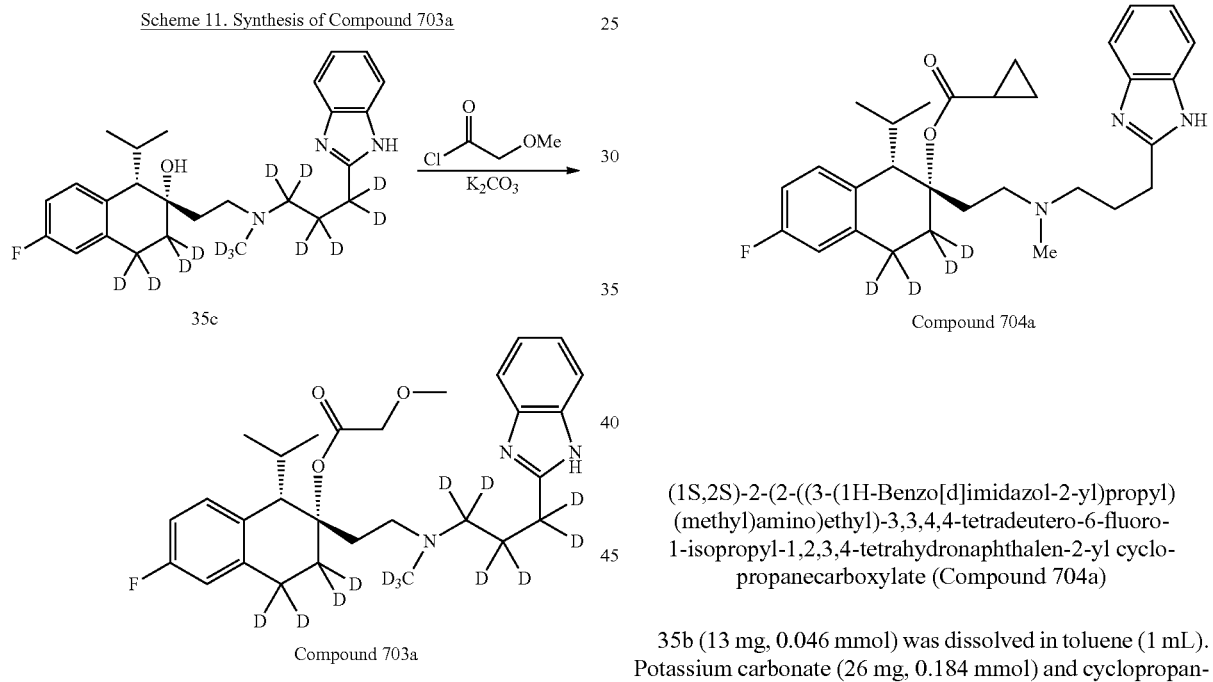

Compound 703a (1S,2S)-2-(2-((3-(1H-Benzo[d]imidazol-2-yl)-1,1,2,2,3,3-hexadeuteropropyl)(trideuteroomethyl)-amino)ethyl)-3,3,4,4-tetradeutero-6-fluoro-1-isopropyl-1,2,3,4-tetrahydronaphthalen-2-yl 2-methoxyacetate (Compound 703a)

Compound 703a was prepared using the method described in Example 4 from 35c (21 mg, 0.048 mmol). Compound 703a was obtained as a colorless oil (17 mg, 0.033 mmol, 69.6% yield). ¹H NMR (400 MHz, CDCl₃): δ 7.50 (m, 2H), 7.20 (m, 2H), 6.93 (m, 1H), 6.81 (m, 1H), 6.76 (m, 1H), 4.04 (q, J=14 Hz, 2H), 3.89 (s, 1H), 3.46 (s, 3H), 3.29 (brs, 1H), 2.94 (m, 1H), 2.70 (m, 1H), 2.35 (m, 1H), 2.0 (m, 1H), 1.60 (m, 1H), 1.05 (d, J=8.0 Hz, 3H), 0.42 (d, J=8.0 Hz, 3H). MS (M+H): 509.4.

Example 6

Synthesis of (1S,2S)-2-(2-((3-(1H-Benzo[d]imidazol-2-yl)propyl)(methyl)amino)ethyl)-3,3,4,4-tetradeutero-6-fluoro-1-isopropyl-1,2,3,4-tetrahydronaphthalen-2-yl cyclopropanecarboxylate (Compound 704a)

Scheme 12. Synthesis of Compound 704a

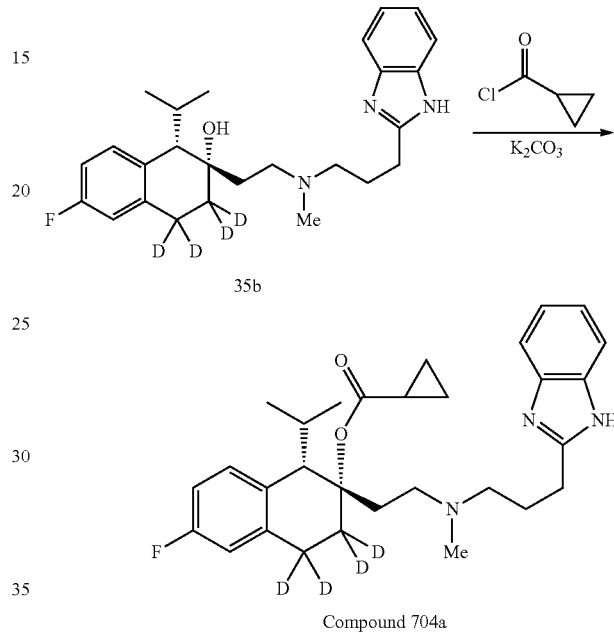

Compound 704a (1S,2S)-2-(2-((3-(1H-Benzo[d]imidazol-2-yl)propyl)(methyl)amino)ethyl)-3,3,4,4-tetradeutero-6-fluoro-1-isopropyl-1,2,3,4-tetrahydronaphthalen-2-yl cyclopropanecarboxylate (Compound 704a)

35b (13 mg, 0.046 mmol) was dissolved in toluene (1 mL). Potassium carbonate (26 mg, 0.184 mmol) and cyclopropanecarbonyl chloride (0.015 mL, 0.164 mmol) were added and the reaction was stirred under a nitrogen atmosphere. After 2 h the mixture was concentrated nearly to dryness and the residue was re-dissolved in a 5% acetic acid/methanol solution (1 mL). The mixture was allowed to stir at ambient temperature until the reaction was deemed complete by LCMS. The mixture was diluted with ethyl acetate and washed with aqueous sodium hydroxide (1N). The organic phase was dried over sodium sulfate, filtered and concentrated to give an oil which was purified on silica gel to afford Compound 704a as a colorless oil (16 mg, 0.032 mmol, 70% yield). ¹H NMR (400 MHz, CDCl₃): δ 7.44 (m, 2H), 7.18 (m, 2H), 6.93 (m, 1H), 6.77 (m, 2H), 4.04 (q, J=14 Hz, 2H), 3.31 (brs, 1H), 3.09 (m, 2H), 2.85 (m, 1H), 2.65 (m, 3H), 2.38 (brs, 4H), 2.08 (m, 3H), 1.93 (m, 1H), 1.62 (m, 2H), 1.04 (d, J=8.0 Hz, 3H), 0.85 (m, 4H), 0.42 (d, J=8.0 Hz, 3H). MS (M+H): 496.4.

Example 7

Synthesis of (1S,2S)-2-(2-((3-(1H-Benzo[d]imidazol-2-yl)-1,1,2,2,3,3-hexadeuteropropyl)(trideuteromethyl)-amino)ethyl)-3,3,4,4-tetradeutero-6-fluoro-1-isopropyl-1,2,3,4-tetrahydronaphthalen-2-yl cyclopropanecarboxylate (Compound 707a)

Scheme 13. Synthesis of Compound 707a.

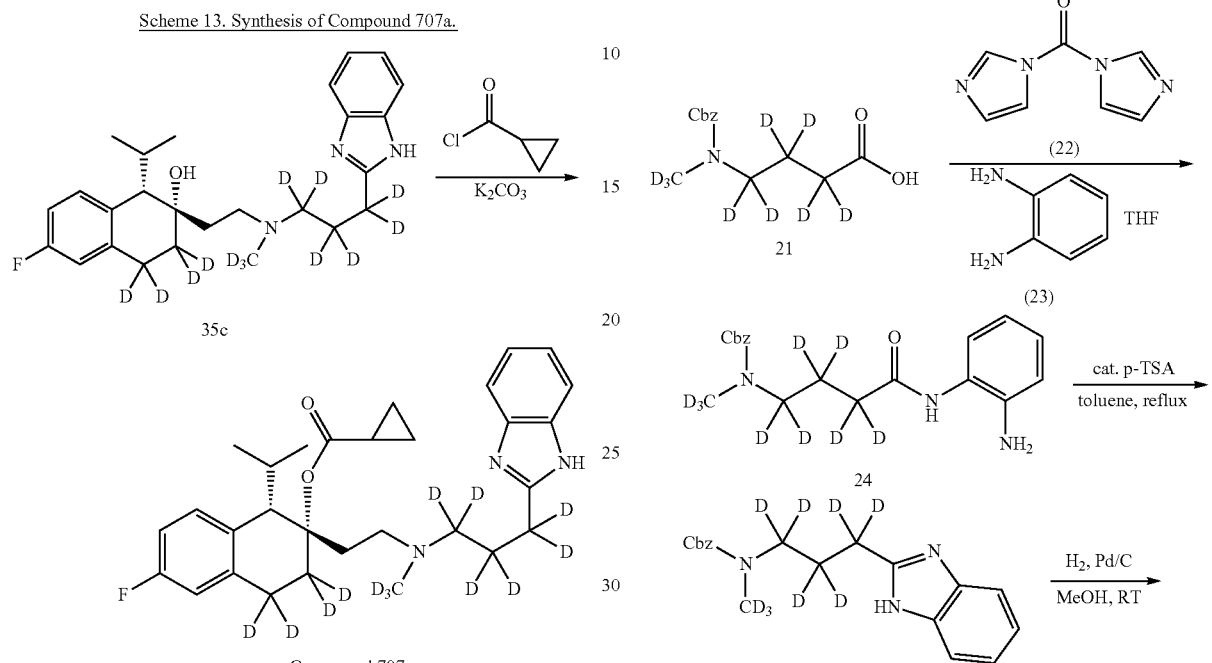

Compound 707a (1S,2S)-2-(2-((3-(1H-Benzo[d]imidazol-2-yl)-1,1,2,2,3,3-hexadeuteropropyl)(trideuteromethyl)-amino)ethyl)-3,3,4,4-tetradeutero-6-fluoro-1-isopropyl-1,2,3,4-tetrahydronaphthalen-2-yl cyclopropanecarboxylate (Compound 707a)

Compound 707a was prepared according to the method described in Example 6 from 35c (26 mg, 0.060 mmol) to yield Compound 707a as a colorless oil (17 mg, 0.034 mmol, 56% yield). $^1$H NMR (400 MHz, CDCl$_3$): δ 7.45 (m, 2H), 7.18 (m, 2H), 6.93 (m, 1H), 6.77 (m, 2H), 4.04 (q, J=14 Hz, 2H), 3.49 (s, 1H), 3.29 (brs, 1H), 3.00 (m, 1H), 2.73 (m, 1H), 2.35 (m, 1H), 2.04 (m, 1H), 1.62 (m, 1H), 1.04 (d, J=8.0 Hz, 3H), 0.89 (m, 4H), 0.42 (d, J=8.0 Hz, 3H). MS (M+H) 505.4.

Example 8

Synthesis of (1S,2S)-2-(2-((3-(1H-Benzo[d]imidazol-2-yl)-1,1,2,2,3,3-hexadeuteropropyl)(trideuteromethyl)-amino)ethyl)-3,3,4,4-tetradeutero-6-fluoro-1-isopropyl-1,2,3,4-tetrahydronaphthalen-2-yl cyclopropanecarboxylate (16a)

Scheme 14. Synthesis of Intermediate 16a.

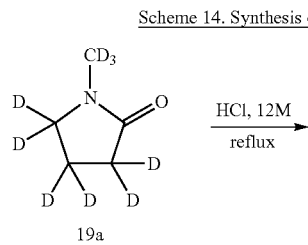

19a

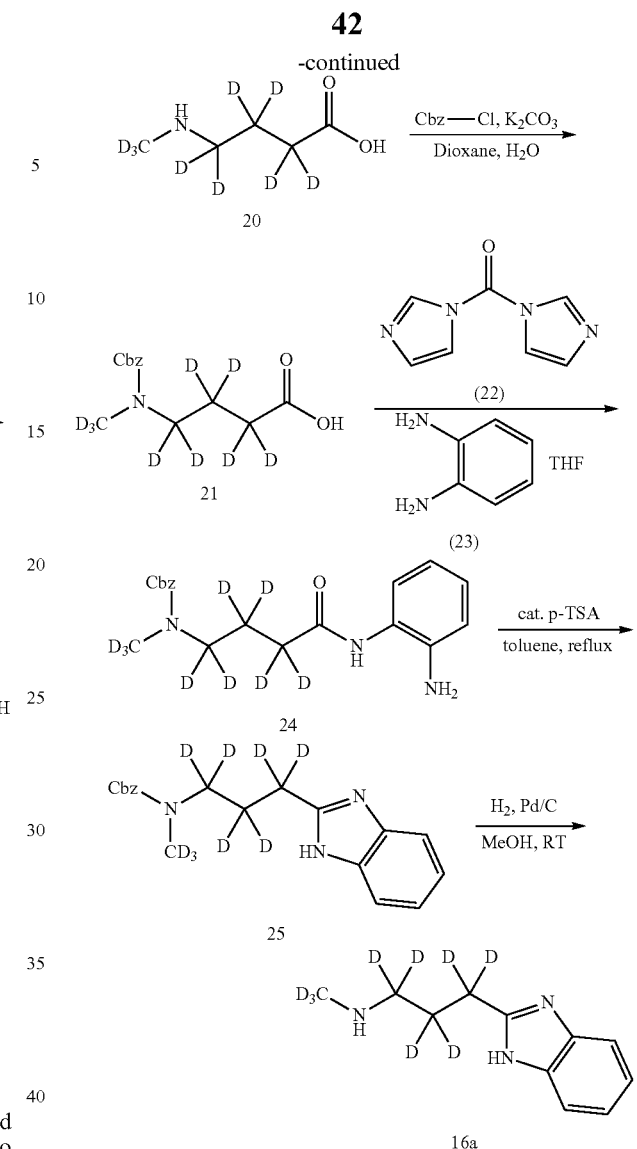

Step 1.
4-(Trideuteromethyl)amino)-2,2,3,3,4,4-butanoic acid (20)

3,3,4,4,5,5-hexadeutero-1-(trideuteromethyl)pyrrolidin-2-one 19a (2.0 g, 18.5 mmol, 98% atom D, CDN Isotopes) was dissolved in deuterium chloride (3 mL, 99% atom D) and heated to a gentle reflux for 12 hours. The reaction was cooled and concentrated to give 2,2,3,3,4,4-hexadeutero-4-((trideuteromethyl)amino)butanoic acid 20 as a tacky white semisolid, which was used in the next step without further purification.

Step 2. 4-(((Benzyloxy)carbonyl)(trideuteromethyl)amino)-2,2,3,3,4,4-hexadeuterobutanoic acid (21)

20 was dissolved in a 4:1 mixture of dioxane and water (100 mL) and cooled to 0° C. Potassium carbonate was added (5.62 g, 40.66) followed by benzyl chloroformate (2.87 mL, 20.3 mmol). The reaction was allowed to warm to ambient temperature over 12 hours. The mixture was then concentrated, and the residue remaining after concentration was re-dissolved in ethyl acetate. The biphasic mixture was separated and the organic phase was washed successively with aqueous saturated sodium bicarbonate solution and brine.

The combined organic solutions were dried over sodium sulfate, filtered, and concentrated to give an orange oil which was purified on ISCO flash chromatography instrument (elution gradient: 0-100% ethyl acetate/heptanes) to yield intermediate 21 as a colorless oil (3.20 g, 12.3 mmol, 66% yield over 2 steps). MS (M+H): 259.2.

Step 3. Benzyl (4-((2-aminophenyl)amino)-1,1,2,2,3,3-hexadeutero-4-oxobutyl)(trideuteromethyl)carbamate (24)

21 (0.5 g, 1.92 mmol) was dissolved in tetrahydrofuran (8 mL) and carbonyldiimidazole (0.24 g, 2.31 mmol) and o-phenylenediamine (0.46 g, 4.22 mmol) were added. The reaction was allowed to warm to ambient temperature over 12 hours. The mixture was concentrated and the residue remaining after concentration re-dissolved in ethyl acetate. The biphasic mixture was separated and the organic phase was washed successively with aqueous saturated ammonium chloride solution and brine. The combined organic solutions were dried over sodium sulfate, filtered, and concentrated to give a yellow oil which was purified on ISCO flash chromatography instrument (elution gradient: 0-100% ethyl acetate/heptanes) to yield intermediate 24 as a colorless oil (220 mg, 0.64 mmol, 33% yield). MS (M+H): 351.2.

Step 4. Benzyl (3-(1H-benzo[d]imidazol-2-yl)-1,1,2,2,3,3-hexachloropropyl)(trichloromethyl)carbamate (25)

24 (296 mg, 0.85 mmol) was dissolved in toluene (85 mL) and p-toluenesulfonic acid (17 mg, 0.09 mmol) was added. The mixture was heated to a gentle reflux for 12 hours, cooled, concentrated and directly transferred to an ISCO column. Purification (elution gradient: 0-100% ethyl acetate/heptanes) yielded intermediate 25 as a colorless oil (239 mg, 0.72 mmol, 85% yield). MS (M+H): 333.2.

Step 5. 3-(1H-Benzo[d]imidazol-2-yl)-1,1,2,2,3,3-hexadeutero-N-(trideuteromethyl)propan-1-amine (16a)

25 (375 mg, 1.13 mmol) was dissolved in methanol (12 mL) and 10% by wt. palladium on carbon (120 mg) was added as a single portion. The reaction was placed under a balloon of hydrogen and allowed to stir for 12 h. The reaction mixture was concentrated and the residue remaining after concentration was re-dissolved in ethyl acetate and filtered through Celite to give intermediate 16a as a white solid (187 mg, 0.944 mmol, 84% yield). MS (M+H): 199.3.

Example 9

Synthesis of (S)-4,4,6-Trifluoro-1-isopropyl-3,4-dihydronaphthalen-2(1H)-one (12b)

Scheme 15. Synthesis of Intermediate 12b.

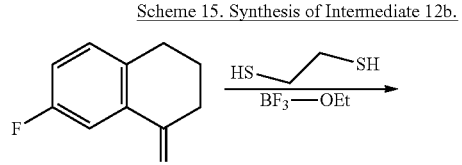

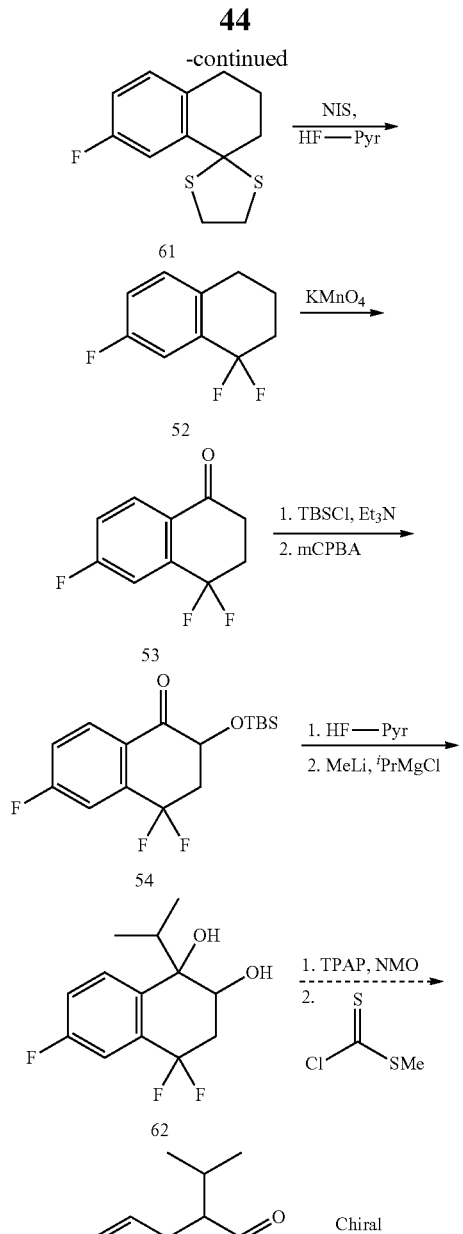

Step 1. 7'-Fluoro-3',4'-dihydro-2'H-spiro[[1,3]dithiolane-2,1'-naphthalene] (61)

Dissolved 7-fluorotetralone, 51 (10.0 g, 60.9 mmol) in 1,2-ethanedithiol (10 mL) and cooled reaction to 0° C. Boron trifluoride diethyl etherate (7.5 mL) was added dropwise. The white suspension became yellow and homogenous. The wet ice bath was removed and the reaction was warmed to ambient temperature. The reaction was then diluted with heptanes (25 mL) and poured into an ice cold solution of saturated sodium bicarbonate. The organic layer was separated, dried over sodium sulfate and concentrated to give colorless oil (14.69 g, 60.9 mmol, 100% yield). $^1$H NMR (400 MHz, CDCl$_3$) δ: 7.60 (d, J=12 Hz, 1H), 6.94 (t, J=4 Hz, 1H), 6.84 (t, J=8 Hz, 1H), 3.56 (m, 2H), 3.46 (m, 2H), 2.75 (m, 2H), 2.37 (m, 2H), 1.99 (m, 2H).

Step 2. 1,1,7-Trifluoro-1,2,3,4-tetrahydronaphthalene (52)

A solution of N-iodosuccinimide (32.3 g, 144.0 mmol) in dichloromethane (260 mL) was cooled to −78° C. in a plastic round bottom flask. A 70% solution of hydrogen fluoride in pyridine (18 mL) followed by a dichloromethane solution (20 mL) of dithiolane 61 (8.65 g, 36.0 mmol) were added dropwise. Upon completion of addition the reaction was warmed to −50° C. and stirred at this temperature for 3 h. The reaction was then poured into ice cold saturated sodium bicarbonate (200 mL) followed by a saturated solution of sodium thiosulfate (150 mL). The colored reaction became colorless and biphasic. The organic phase was separated, dried (sodium sulfate) and concentrated to give a yellow oil. The product was purified by silica gel chromatography with a gradient heptanes/ethyl acetate eluent system on an ISCO companion system to give the desired product as a yellow oil (3.11 g, 16.7 mmol, 46% yield). $^1$H NMR (400 MHz, CDCl$_3$) δ: 7.34 (d, J=8 Hz, 1H), 7.07 (m, 1H), 7.05 (m, 1H), 2.80 (brs, 2H), 2.26 (m, 2H), 1.99 (m, 2H); $^{19}$F NMR (400 MHz, CDCl$_3$) δ: −91.7 (s, 2H), −122.8 (s, 1H).

Step 3. 4,4,6-Trifluoro-3,4-dihydronaphthalen-1(2H)-one (53)

An acetone solution (278 mL) of trifluoride 52 (3.11 g, 16.7 mmol) was diluted with an aqueous solution (209 mL) of magnesium sulfate heptahydrate (12.4 g). The solution was then cooled to 0° C. and potassium permanganate (7.92 g) was added portion wise over 1 hour. The reaction was allowed to warm to ambient temperature over 16 h. The reaction was quenched by addition of an aqueous 50% citric acid solution (100 mL) followed by sodium thiosulfate (5.21 g). The dark purple reaction became colorless and biphasic. The volatiles were removed and the aqueous was then extracted with dichloromethane (300 mL). The organic phase was separated, dried over sodium sulfate and concentrated. The product was purified by silica gel with a gradient heptanes/ethyl acetate eluent system on an ISCO companion to give the desired product as a yellow oil (2.09 g, 10.4 mmol, 63% yield). $^1$H NMR (400 MHz, CDCl$_3$) δ: 8.10 (t, J=8 Hz, 1H), 7.44 (d, J=4 Hz, 1H), 7.26 (m, 1H), 2.91 (t, J=4 Hz, 2H), 2.66 (m, 2H).

Step 4. 2-((tert-Butyldimethylsilyl)oxy)-4,4,6-trifluoro-3,4-dihydronaphthalen-1(2H)-one (54)

Triethylamine (1.97 mL, 14.2 mmol) followed by tert-butyldimethylsilyl trifluoromethanesulfonate (1.63 mL) were added dropwise to a dichloroethane solution (16 mL) of ketone 53 (0.945 g, 4.72 mmol). After thirty minutes the reaction was quenched with silica gel (3.0 g), concentrated and purified on an ISCO companion with a gradient heptanes/ethyl acetate eluent system to give the silyl enol ether as a yellow oil (1.51 g). The silyl enol ether was dissolved in dichloroethane (24 mL) and cooled to −20° C. A dichloroethane solution (5 mL) of meta-chloroperoxy benzoic acid (1.28 g, 5.19 mmol) was added dropwise. The reaction was warmed to ambient temperature and stirred for ninety minutes. The reaction was then poured into a saturated solution of sodium bicarbonate and the aqueous was back extracted with dichloromethane. The combined organics were dried over sodium sulfate and filtered. Imidazole (0.482 g) and tert-butyldimethylsilyl chloride (0.783 g) were added to the dichloromethane solution. After 12 h the reaction mixture was poured into an aqueous solution of ammonium chloride and the aqueous phase was back extracted with dichloromethane. The combined organics were dried over sodium sulfate, filtered, and concentrated to give an orange oil. The desired product was purified with a gradient heptanes/ethyl acetate eluent system on silica gel by a ISCO companion system to give the desired product as a colorless oil (1.0 g, 3.03 mmol, 64% yield). $^1$H NMR (400 MHz, CDCl$_3$) δ: 8.12 (dd, J=8, 4 Hz, 1H), 7.44 (dt, J=8, 4 Hz, 1H), 7.28 (m, 1H), 4.66 (ddd, J=12, 8, 4 Hz, 1H), 2.95 (m, 1H), 2.70 (m, 1H), 0.97 (s, 9H), 0.25 (s, 3H), 0.16 (s, 3H).

Step 5. 4,4,6-Trifluoro-1-isopropyl-1,2,3,4-tetrahydronaphthalene-1,2-diol (62)

A THF solution (8 mL) of 2-((tert-butyldimethylsilyl)oxy)-4,4,6-trifluoro-3,4-dihydronaphthalen-1(2H)-one 54 (0.585 g, 1.77 mmol) was cooled to 0° C. and a solution of hydrogen fluoride in pyridine (70%, 200 μL) was added dropwise. The reaction was allowed to warm to ambient temperature over 12 h at which point the reaction was quenched with an aqueous solution of saturated sodium bicarbonate, volatiles were removed and the mixture was re-dissolved in ethyl acetate. The aqueous phase was extracted with ethyl acetate (3×), dried over sodium sulfate, filtered and concentrated to give an orange oil. The desired product, 4,4,6-trifluoro-2-hydroxy-3,4-dihydronaphthalen-1(2H)-one, was purified with a gradient heptanes/ethyl acetate eluent system on silica gel by a ISCO companion system to give the desired product as a colorless oil (0.263 g, 1.22 mmol, 69% yield). $^1$H NMR (400 MHz, CDCl$_3$) δ: 8.14 (dd, J=8, 4 Hz, 1H), 7.48 (dt, J=8, 4 Hz, 1H), 7.36 (m, 1H), 4.67 (ddd, J=12, 8, 4 Hz, 1H), 3.66 (s, 1H), 3.17 (m, 1H), 2.54 (m, 1H).

A THF solution (3.75 mL) of methyl lithium (3.05 mL, 4.88 mmol) was cooled to −78° C. with a dry ice/acetone cooling bath. A hexanes solution of isopropyl magnesium chloride (1.44 mL, 2.68 mmol) was introduced by syringe. This mixture was allowed to age for one hour at this temperature. Then a THF solution (1.75 mL) of 4,4,6-trifluoro-2-hydroxy-3,4-dihydronaphthalen-1(2H)-one (0.263 mg, 1.22 mmol) was added to the cooled solution dropwise by syringe pump over one hour. The reaction was allowed to stir at −78° C. for 4 hours and then quenched by pouring into an aqueous solution of ammonium chloride, volatiles were removed and the mixture was re-dissolved in ethyl acetate. The aqueous phase was extracted with ethyl acetate (3×), dried over sodium sulfate, filtered and concentrated to give an orange oil. The desired product, 4,4,6-trifluoro-2-hydroxy-3,4-dihydronaphthalen-1(2H)-one, was purified with a gradient heptanes/ethyl acetate eluent system on silica gel by a ISCO companion system to give the desired product, 4,4,6-trifluoro-1-isopropyl-1,2,3,4-tetrahydronaphthalene-1,2-diol, as a colorless oil (0.189 g, 0.727 mmol, 60% yield). $^1$H NMR (400 MHz, CDCl$_3$) δ: 7.65 (m, 1H), 7.34 (d, J=8 Hz, 1H), 7.19 (m, 1H), 4.32 (m, 1H), 2.69 (m, 2H), 1.96 (q, J=8 Hz, 1H) 0.98 (d, J=4 Hz, 1H) 0.93 (d, J=4 Hz, 1H). MS (ESI−, infusion) 259 [(M−H)⁻].

Step 6. 4,4,6-trifluoro-1-isopropyl-3,4-dihydronaphthalen-2(1H)-one (63)

Diol 62 is converted to ketone 63 via treatment with TPAP followed by methyl carbonochloridodithioate.

Step 7. (S)-4,4,6-Trifluoro-1-isopropyl-3,4-dihydronaphthalen-2(1H)-one (12b)

Intermediate 12b is isolated through routine chiral separation of the separate enantiomers of 63.

Example 10

(1S,2R)-2-(2-((3-(1H-Benzo[d]imidazol-2-yl)propyl)(methyl)amino)ethyl)-4,4,6-trifluoro-1-isopropyl-1,2,3,4-tetrahydronaphthalen-2-ol (35d)

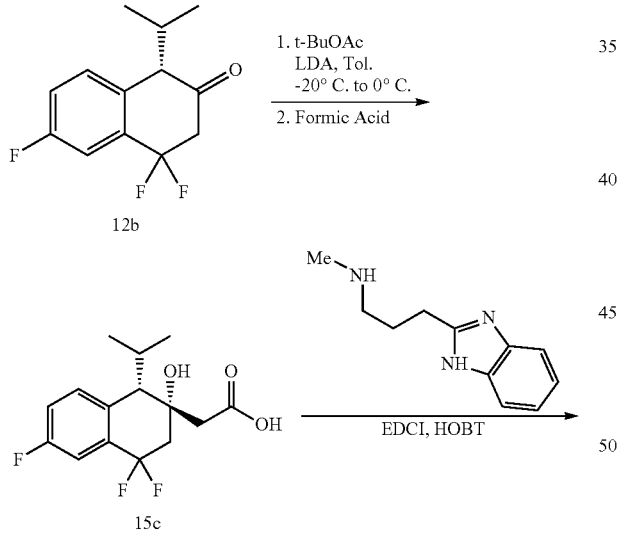

Step 1. 2-((1S,2R)-4,4,6-Trifluoro-2-hydroxy-1-isopropyl-1,2,3,4-tetrahydronaphthalen-2-yl)acetic acid (15c)

Carboxylic acid 15c is prepared from 12b in a manner analogous to that of Example 1, step 2 for acid 15b.

Step 2. N-(3-(1H-Benzo[d]imidazol-2-yl)propyl)-N-methyl-2-((1S,2R)-4,4,6-trifluoro-2-hydroxy-1-isopropyl-1,2,3,4-tetrahydronaphthalen-2-yl)acetamide (17d)

Intermediate 17d is prepared from 15c and 16e in a manner analogous to that of Example 2, step 1 for 17b.

Step 3. (1S,2R)-2-(2-((3-(1H-Benzo[d]imidazol-2-yl)propyl)(methyl)amino)ethyl)-4,4,6-trifluoro-1-isopropyl-1,2,3,4-tetrahydronaphthalen-2-ol (35d)

35d is prepared from 17d in a manner analogous to that of Example 2, step 2 for 35b.

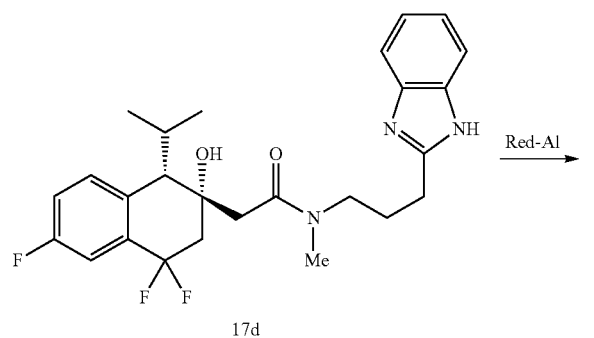

Example 11

(1S,2R)-2-(2-((3-(1H-Benzo[d]imidazol-2-yl)-1,1,2,2,3,3-hexadeuteropropyl)(trideuteromethyl)amino)ethyl)-4,4,6-trifluoro-1-isopropyl-1,2,3,4-tetrahydronaphthalen-2-ol (35e)

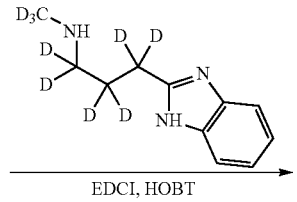

-continued

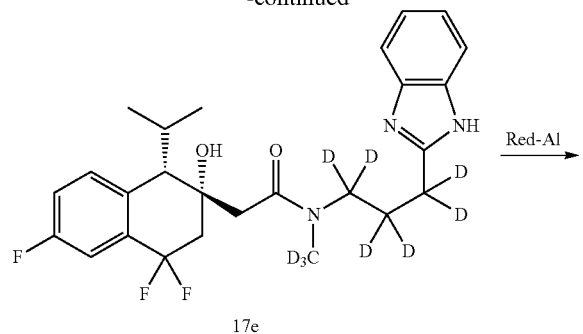

17e

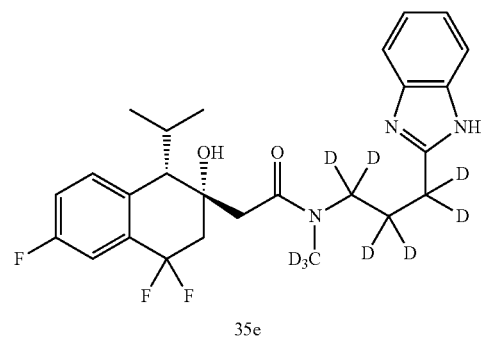

35e

Step 1. N-(3-(1H-Benzo[d]imidazol-2-yl)-1,1,2,2,3,3-hexadeuteropropyl)-N-(trideuteromethyl)-2-((1S,2R)-4,4,6-trifluoro-2-hydroxy-1-isopropyl-1,2,3,4-tetrahydronaphthalen-2-yl)acetamide (17e)

Intermediate 17e is prepared from 15c and 16e in a manner analogous to that of Example 3, step 1 for 17c.

Step 2. (1S,2R)-2-(2-((3-(1H-Benzo[d]imidazol-2-yl)-1,1,2,2,3,3-hexadeuteropropyl)(trideuteromethyl)amino)-ethyl)-4,4,6-trifluoro-1-isopropyl-1,2,3,4-tetrahydronaphthalen-2-ol (35e)

35e is prepared from 17e in a manner analogous to that of Example 3, step 2 for 35c.

Example 12

(1S,2R)-2-(2-(3-(1H-Benzo[d]imidazol-2-yl)propyl)(methyl)amino)ethyl)-4,4,6-trifluoro-1-isopropyl-1,2,3,4-tetrahydronaphthalen-2-yl 2-methoxyacetate (Compound 104)

Scheme 18. Synthesis of Compound 104.

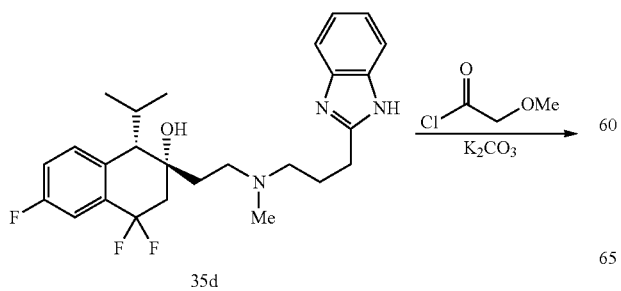

35d

-continued

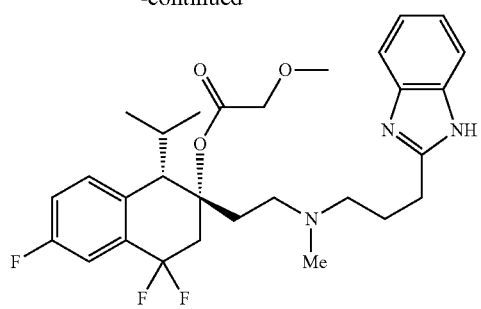

104

(1S,2R)-2-(2-((3-(1H-Benzo[d]imidazol-2-yl)propyl)(methyl)amino)ethyl)-4,4,6-trifluoro-1-isopropyl-1,2,3,4-tetrahydronaphthalen-2-yl 2-methoxyacetate (Compound 104): Compound 104 is prepared from 35d in a manner analogous to that of Example 4 for compound 500.

Example 13

(1S,2R)-2-(2-(3-(1H-Benzo[d]imidazol-2-yl)propyl)(methyl)amino)ethyl)-4,4,6-trifluoro-1-isopropyl-1,2,3,4-tetrahydronaphthalen-2-yl cyclopropanecarboxylate (Compound 304)

Scheme 19. Synthesis of Compound 304.

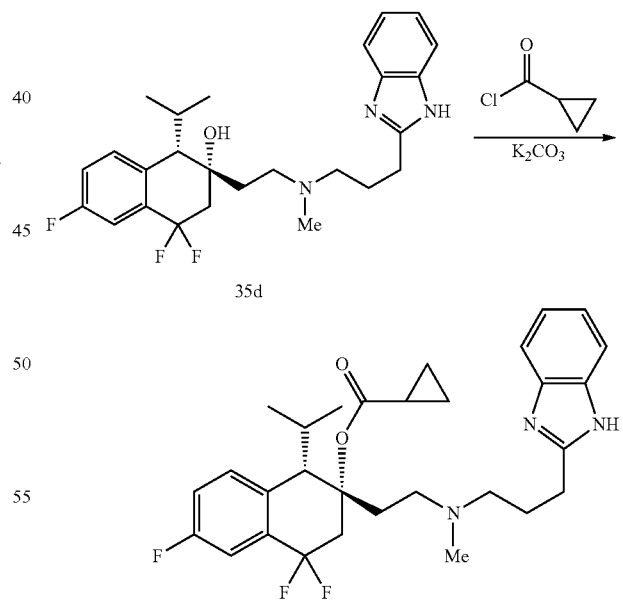

(1S,2R)-2-(2-((3-(1H-Benzo[d]imidazol-2-yl)propyl)(methyl)amino)ethyl)-4,4,6-trifluoro-1-isopropyl-1,2,3,4-tetrahydronaphthalen-2-yl cyclopropanecarboxylate (Compound 304): Compound 304 is prepared from 35d in a manner analogous to that of Example 6 for compound 704a.

Example 14

(1S,2R)-2-(2-(3-(1H-Benzo[d]imidazol-2-yl)-1,1,2,2,3,3-hexadeuteropropyl)(trideuteromethyl)amino)-ethyl)-4,4,6-trifluoro-1-isopropyl-1,2,3,4-tetrahydronaphthalen-2-yl 2-methoxyacetate (Compound 622)

Scheme 20. Synthesis of Compound 622.

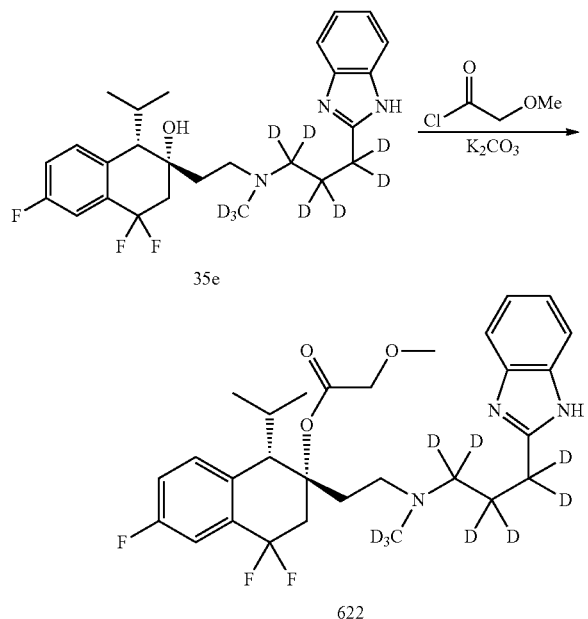

(1S,2R)-2-(2-((3-(1H-Benzo[d]imidazol-2-yl)-1,1,2,2,3,3-hexadeuteropropyl)(trideuteromethyl)amino)-ethyl)-4,4,6-trifluoro-1-isopropyl-1,2,3,4-tetrahydronaphthalen-2-yl 2-methoxyacetate (Compound 622): Compound 622 is prepared from 35e in a manner analogous to that of Example 4 for compound 500.

Example 15

(1S,2R)-2-(2-(3-(1H-Benzo[d]imidazol-2-yl)-1,1,2,2,3,3-hexadeuteropropyl)(trideuteromethyl)amino)-ethyl)-4,4,6-trifluoro-1-isopropyl-1,2,3,4-tetrahydronaphthalen-2-yl cyclopropanecarboxylate (Compound 808a)

Scheme 21. Synthesis of Compound 808a.

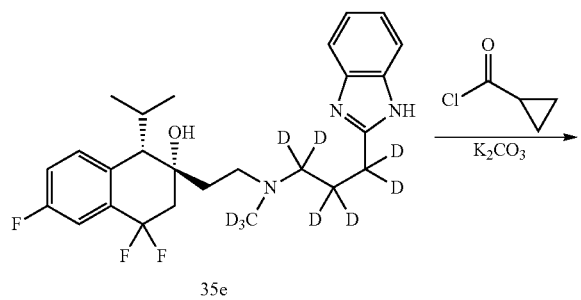

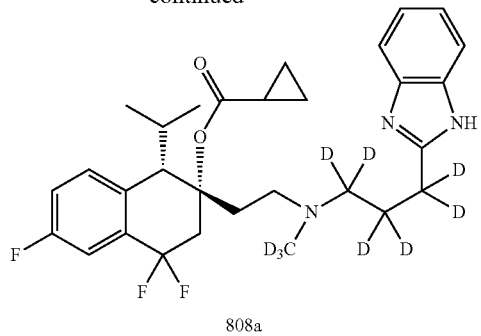

(1S,2R)-2-(2-(3-(1H-Benzo[d]imidazol-2-yl)-1,1,2,2,3,3-hexadeuteropropyl)(trideuteromethyl)amino)-ethyl)-4,4,6-trifluoro-1-isopropyl-1,2,3,4-tetrahydronaphthalen-2-yl cyclopropanecarboxylate (Compound 808a): Compound 808a is prepared from 35e in a manner analogous to that of Example 6 for compound 704a.

Example 16

Investigation of CYP3A4 Mechanism-Based Inhibition by Mibefradil and D-Mibefradils Using Testosterone as the CYP3A4 Marker Substrate Human liver microsomes (final concentration 0.13 mg/mL) were pre-incubated with test compounds mibefradil, 500, and 703a for 0 min, 1 min, and 3 min each. The concentrations of the test compounds were: 0.2, 0.3, 0.4, 0.5, 0.6, 0.8, 1, 2, 3, 4, and 5 µM. After the pre-incubation, the samples were diluted 1:10 into buffer containing 200 µM testosterone and 2 mM NADPH and these mixture were incubated for another 10 minutes. Incubations were stopped with acetonitrile containing an internal standard. Samples were then centrifuged at 3000 rpm for 10 minutes and the supernatant were analyzed for the formation of 6-β-hydroxy testosterone by LC-MS/MS.

The inactivation rate constants ($k_{obs}$) were determined from the initial slopes of plots of LN (CYP activity) remaining versus preincubation time. The $k_{inact}$ and $K_I$ values were estimated from plots of $k_{obs}$ versus inhibitor concentration by non-linear regression analysis using GraphPad Prism v5.01, according to the equation shown below:

$$K_{obs} = k_{inact} * X/(K_I + X)$$

where X is the inhibitor concentration.

Example 17

Evaluation of Metabolic Stability

Microsomal Assay:
Human liver microsomes (20 mg/mL) were obtained from Xenotech, LLC (Lenexa, Kans.). β-nicotinamide adenine dinucleotide phosphate, reduced form (NADPH), magnesium chloride (MgCl$_2$), and dimethyl sulfoxide (DMSO) were purchased from Sigma-Aldrich.

Determination of Metabolic Stability:
7.5 mM stock solutions of test compounds were prepared in DMSO. The 7.5 mM stock solutions were diluted to 12.5-50 µM in acetonitrile (ACN). The 20 mg/mL human liver microsomes were diluted to 0.625 mg/mL in 0.1 M potassium phosphate buffer, pH 7.4, containing 3 mM MgCl$_2$. The diluted microsomes were added to wells of a 96-well deepwell polypropylene plate in triplicate. A 10 µL aliquot of the 12.5-50 µM test compound was added to the microsomes and the mixture was pre-warmed for 10 minutes. Reactions were initiated by addition of pre-warmed NADPH solution. The final reaction volume was 0.5 mL and contained 0.5 mg/mL human liver microsomes, 0.25-1.0 µM test compound, and 2 mM NADPH in 0.1 M potassium phosphate buffer, pH 7.4, and 3 mM $MgCl_2$. The reaction mixtures were incubated at 37° C., and 50 µL aliquots were removed at 0, 5, 10, 20, and 30 minutes and added to shallow-well 96-well plates which contained 50 µL of ice-cold ACN with internal standard to stop the reactions. The plates were stored at 4° C. for 20 minutes after which 100 µL of water was added to the wells of the plate before centrifugation to pellet precipitated proteins. Supernatants were transferred to another 96-well plate and analyzed for amounts of parent remaining by LC-MS/MS using an Applied Bio-systems API 4000 mass spectrometer. The same procedure was followed for the non-deuterated counterpart of the compound of Formula B, Formula A, Formula I, Formula B-I, Formula C, or Formula E and the positive control, 7-ethoxycoumarin (1.0 µM). Testing was done in triplicate.

Data Analysis:

The in vitro $t_{1/2}$s for test compounds were calculated from the slopes of the linear regression of % parent remaining (ln) vs incubation time relationship.

$$\text{in vitro } t_{1/2} = 0.693/k$$

$k=-$[slope of linear regression of % parent remaining (ln) vs incubation time]

Data analysis was performed using Microsoft Excel Software.

The results of the mechanism-based inhibition (MBI) study in human liver microsomes (HLM) are shown in FIG. 1 and in Table 7 below. As both FIG. 1 and the table show, CYP3A4 mechanism-based inhibition of compound 500 and compound 703a is markedly reduced relative to mibefradil.

TABLE 7

Results of In Vitro MBI Studies in HLM

| Compound | $K_i$ (µM) | $k_{inact}$ (µM) |
|---|---|---|
| Mibefradil | 0.66 ± 0.18[a] | 0.37 ± 0.11[a] |
| 500 | Not calculable | Not calculable |
| 703a | Not calculable | Not calculable |

[a]average ± SD, N = 3 experiments. Literature values for Mibefradil according to Preuksaritanont, T. et al., Br. J. Clin. Pharmacol. 1999, 47, 291-298: $K_I$ = 2.3 µM, $k_{inact}$ = 0.4 min$^{-1}$, Partition ratio = 1.7

The results of the human liver microsome study are shown in the tables below.

TABLE 8a

Results of In Vitro HLM Studies for deuterated-Mibefradil

| | $t_{1/2}$ (min) | | |
|---|---|---|---|
| Compound | Experiment 1 | Experiment 2 | Ave |
| Mibefradil | 8.49 | 8.55 | 8.52 |
| 500 | 4.61 | 4.98 | 4.79 |
| 703a | 7.17 | 7.72 | 7.45 |

TABLE 8b

Results of In Vitro HLM Studies for deuterated-NNC 55-0396[1]

| | $t_{1/2}$ (min) | | |
|---|---|---|---|
| Compound | Experiment 1 | Experiment 2 | Ave |
| NNC 55-0396 | 6.58 | 6.55 | 6.56 |
| 704a | 6.16 | 6.60 | 6.38 |
| 707a | 7.27 | 7.03 | 7.15 |

[1]The structure of NNC 55-0396 is:

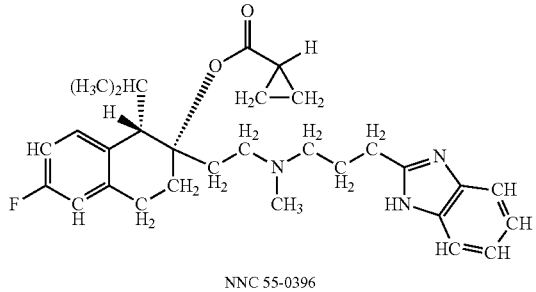

NNC 55-0396

The results of the human liver microsome study, as shown in Table 8a above, reveal that the half life ($t_{1/2}$) of compound 500 is approximately 44% shorter than that of mibefradil. This result further supports the showing above of reduction/removal of mechanism based inhibition for compound 500 relative to mibefradil.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

We claim:

1. A compound of Formula (I):

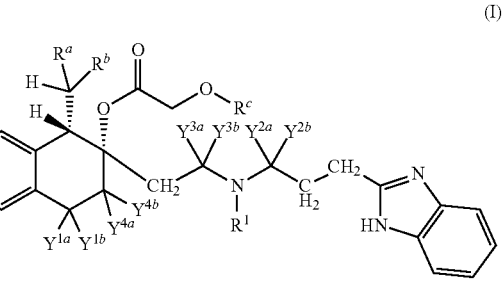

or a pharmaceutically acceptable salt thereof, wherein:
 $R^a$, $R^b$ and $R^c$ are each independently selected from —$CH_3$ and —$CD_3$;
 $Y^{1a}$ and $Y^{1b}$ are each deuterium;
 $Y^{2a}$ and $Y^{2b}$ are the same and are selected from hydrogen and deuterium;
 $Y^{3a}$ and $Y^{3b}$ are each independently selected from hydrogen and deuterium;
 $Y^{4a}$ and $Y^{4b}$ are each deuterium;
 and
 $R^1$ is selected from —$CH_3$ and —$CD_3$;
wherein any atom not designated as deuterium is present at its natural isotopic abundance.

2. The compound of claim 1, wherein:
$R^a$, $R^b$ and $R^c$ are each —$CH_3$.

3. The compound of claim 1 wherein $R^1$ is —$CD_3$.

4. The compound of claim 1, wherein $R^1$ is —$CH_3$.

5. The compound of claim 1, wherein $Y^{2a}$ and $Y^{2b}$ are each hydrogen.

6. The compound of claim 1, wherein $Y^{2a}$ and $Y^{2b}$ are each deuterium.

7. The compound of claim 2, wherein $R^1$ is —$CD_3$; and $Y^{2a}$ and $Y^{2b}$ are each hydrogen.

8. The compound of claim 2, wherein $R^1$ is —$CD_3$; and $Y^{2a}$ and $Y^{2b}$ are each deuterium.

9. The compound of claim 2, wherein the compound is selected from any one of the compounds in the table below:

| Cmpd # | $Y^{1a}$ and $Y^{1b}$ | $R^1$ | $Y^{2a}$ and $Y^{2b}$ | $Y^{3a}$ and $Y^{3b}$ |
|---|---|---|---|---|
| 500 | D | $CH_3$ | H | H |
| 511 | D | $CH_3$ | H | D |
| 512 | D | $CD_3$ | H | D |
| 513 | D | $CH_3$ | D | D |
| 514 | D | $CD_3$ | D | D | or a pharmaceutically acceptable salt thereof.

10. A pyrogen free pharmaceutical composition comprising a compound of claim 1 or a pharmaceutically acceptable salt thereof, and a pharmaceutically acceptable carrier.

11. The composition of claim 10, additionally comprising a therapeutic agent selected from a beta blocker, an aldose reductase inhibitor, a NSAID, a $5HT_{1D}$ agonist, a dopamine D2 receptor antagonist, a secale alkaloid, a second calcium channel blocker and a neurokinin antagonist.

12. A compound of Formula A:

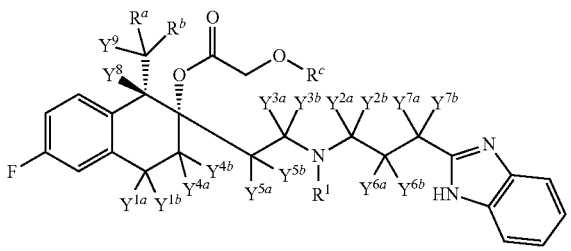

(A)

or a pharmaceutically acceptable salt thereof, wherein:
$R^a$, $R^b$ and $R^c$ are each independently selected from —$CH_3$ and —$CD_3$;
$Y^{1a}$ and $Y^{1b}$ are each deuterium;
$Y^{2a}$ and $Y^{2b}$ are each independently selected from hydrogen and deuterium;
$Y^{3a}$ and $Y^{3b}$ are each independently selected from hydrogen and deuterium;
$Y^{4a}$ and $Y^{4b}$ are each deuterium;
$Y^{5a}$ and $Y^{5b}$ are each independently selected from hydrogen and deuterium;
$Y^{6a}$ and $Y^{6b}$ are each independently selected from hydrogen and deuterium;
$Y^{7a}$ and $Y^{7b}$ are each independently selected from hydrogen and deuterium;
$Y^8$ is hydrogen;
$Y^9$ is hydrogen;
and
$R^1$ is selected from —$CH_3$ and —$CD_3$;
and wherein any atom not designated as deuterium is present at its natural isotopic abundance.

13. A compound of claim 12 wherein $R^a$, $R^b$ and $R^c$ are each —$CH_3$; $Y^{2a}$ and $Y^{2b}$ are the same; $Y^{5a}$ and $Y^{5b}$ are each hydrogen; $Y^{6a}$ and $Y^{6b}$ are each deuterium; $Y^{7a}$ and $Y^{7b}$ are each deuterium, and the compound is selected from any one of the compounds in the table below:

| Cmpd # | $Y^{1a}$ and $Y^{1b}$ | $R^1$ | $Y^{2a}$ and $Y^{2b}$ | $Y^{3a}$ and $Y^{3b}$ |
|---|---|---|---|---|
| 611 | D | $CH_3$ | H | D |
| 612 | D | $CD_3$ | H | D |
| 613 | D | $CH_3$ | D | D |
| 614 | D | $CD_3$ | D | D | or a pharmaceutically acceptable salt thereof.

14. A pyrogen free pharmaceutical composition comprising a compound of claim 12 or a pharmaceutically acceptable salt thereof, and a pharmaceutically acceptable carrier.

15. A compound of Formula C:

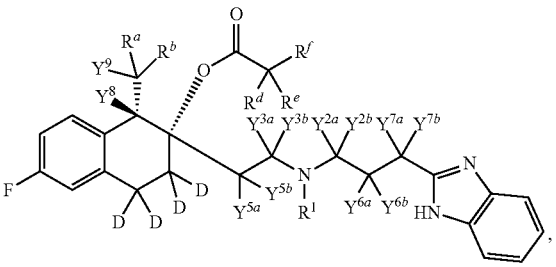

(C)

or a pharmaceutically acceptable salt thereof, wherein
$R^a$ and $R^b$ are each independently selected from —$CH_3$ and —$CD_3$;
$R^d$ and $R^e$ are each hydrogen;
$R^f$ is $OR^c$ wherein $R^c$ is —$CH_3$;
$Y^{3a}$ and $Y^{3b}$ are each independently selected from hydrogen and deuterium;
$Y^{5a}$ and $Y^{5b}$ are each independently selected from hydrogen and deuterium;
$Y^8$ is hydrogen;
$Y^9$ is hydrogen;
$R^1$ is selected from —$CH_3$ and —$CD_3$; and
each of $Y^{2a}$, $Y^{2b}$, $Y^{6a}$, $Y^{6b}$, $Y^{7a}$ and $Y^{7b}$ is the same and is either hydrogen or deuterium, and wherein any atom not designated as deuterium is present at its natural isotopic abundance.

16. The compound of claim 15, wherein the compound is selected from any one of the compounds set forth in the table below, wherein $R^a$ and $R^b$ are each —$CH_3$, and each of $Y^{3a}$, $Y^{3b}$, $Y^{5a}$, and $Y^{5b}$ is deuterium:

| Cmpd # | $R^1$ | Each of $Y^{2a}$, $Y^{2b}$, $Y^{6a}$, $Y^{6b}$, $Y^{7a}$ and $Y^{7b}$ | $R^d$ $R^e$ $R^f$ |
|---|---|---|---|
| 700b | $CH_3$ | H | $CH_2OCH_3$ |
| 701b | $CH_3$ | D | $CH_2OCH_3$ |
| 700b | $CH_3$ | H | $CH_2OCH_3$ |

-continued

| Cmpd # | $R^1$ | Each of $Y^{2a}, Y^{2b}, Y^{6a}, Y^{6b}, Y^{7a}$ and $Y^{7b}$ | $R^d$ | $R^e$ (with $R^f$) |
|---|---|---|---|---|
| 702b | $CD_3$ | H | | $CH_2OCH_3$ |
| 703b | $CD_3$ | D | | $CH_2OCH_3$ | or a pharmaceutically acceptable salt thereof.

17. A pyrogen free pharmaceutical composition comprising a compound of claim 15 or a pharmaceutically acceptable salt thereof, and a pharmaceutically acceptable carrier.

18. The compound of claim 15, wherein the compound is selected from any one of the compounds set forth in the table below, wherein $R^a$ and $R^b$ are each —$CH_3$, and each of $Y^{3a}$, $Y^{3b}$, $Y^{5a}$, and $Y^{5b}$ is hydrogen:

| Cmpd # | $R^1$ | Each of $Y^{2a}, Y^{2b}, Y^{6a}, Y^{6b}, Y^{7a}$ and $Y^{7b}$ | $R^d$ | $R^e$ (with $R^f$) |
|---|---|---|---|---|
| 701a | $CH_3$ | D | | $CH_2OCH_3$ |
| 702a | $CD_3$ | H | | $CH_2OCH_3$ |
| 703a | $CD_3$ | D | | $CH_2OCH_3$ | or a pharmaceutically acceptable salt thereof.

19. The compound of claim 1, wherein the deuterium incorporation at each atom designated as deuterium is at least 90%.

20. The compound of claim 12, wherein the deuterium incorporation at each atom designated as deuterium is at least 90%.

21. The compound of claim 15, wherein the deuterium incorporation at each atom designated as deuterium is at least 90%.

* * * * *